US 7,846,201 B2

(12) United States Patent
Chorny et al.

(10) Patent No.: US 7,846,201 B2
(45) Date of Patent: Dec. 7, 2010

(54) MAGNETICALLY-DRIVEN BIODEGRADABLE GENE DELIVERY NANOPARTICLES FORMULATED WITH SURFACE-ATTACHED POLYCATIONIC COMPLEX

(75) Inventors: Michael Chorny, Philadelphia, PA (US);
Boris Polyak, Philadelphia, PA (US);
Ilia Fishbein, Philadelphia, PA (US);
Ivan Alferiev, Clementon, NJ (US);
Robert J. Levy, Merion Station, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 1454 days.

(21) Appl. No.: 11/250,948

(22) Filed: Oct. 14, 2005

(65) Prior Publication Data
US 2006/0057211 A1 Mar. 16, 2006

Related U.S. Application Data

(63) Continuation-in-part of application No. PCT/US2004/011861, filed on Apr. 16, 2004.

(60) Provisional application No. 60/546,233, filed on Feb. 20, 2004.

(51) Int. Cl.
*A61F 2/02* (2006.01)
(52) U.S. Cl. ................ 623/1.42; 424/646; 600/12; 604/507
(58) Field of Classification Search .................. None
See application file for complete search history.

(56) References Cited

U.S. PATENT DOCUMENTS 3,474,777 A * 10/1969 Figge et al. ................ 424/1.29

(Continued)

FOREIGN PATENT DOCUMENTS

WO    WO 00/43044 A1 *   7/2000

OTHER PUBLICATIONS

Christian Plank, Ulrike Schillinger, Franz Acherer, Christian Bergemann, Jean-Serge Remy, Florian Krotz, Martina Anton, Jim Lausier and Joseph Rosenecker, The Magnetofection Method: Using Magnetic Force to Enhance Gene Delivery, May 2003, Biol. Chem., vol. 384, pp. 737-747, Walter de Gruyter, Berlin, New York.

(Continued)

*Primary Examiner*—Paul Prebilic
(74) *Attorney, Agent, or Firm*—RatnerPrestia

(57) ABSTRACT

A particle including a matrix-forming agent and a polyelectrolyte-amphiphilic agent adduct wherein the polyelectrolyte-amphiphilic agent adduct is in physical communication with the matrix-forming agent. The particle further includes a coated magnetic field-responsive agent and a biomaterial. Methods of making the particle are provided. Also provided are methods of delivery of the biomaterial to a target cell or a target tissue including administering the particle having the matrix-forming agent, polyelectrolyte-amphiphilic agent adduct, the coated magnetic field-responsive agent and the biomaterial; providing a magnetic device associated with the target cell or the target tissue; applying a magnetic force to the particle; and guiding the particle toward the magnetic device by the magnetic force.

21 Claims, 10 Drawing Sheets

U.S. PATENT DOCUMENTS

| | | | | |
|---|---|---|---|---|
| 4,176,058 | A | * | 11/1979 | Grobler ...................... 210/632 |
| 4,345,588 | A | * | 8/1982 | Widder et al. .................. 600/12 |
| 4,465,518 | A | * | 8/1984 | Miyoshi et al. ............. 106/715 |
| 4,501,726 | A | * | 2/1985 | Schroder et al. ........... 424/1.37 |
| 5,665,333 | A | * | 9/1997 | Homola et al. ................. 424/54 |
| 5,843,509 | A | * | 12/1998 | Calvo Salve et al. ........ 424/489 |
| 5,889,110 | A | * | 3/1999 | Hutchinson ................ 525/54.1 |
| 5,916,539 | A | | 6/1999 | Pilgrimm |
| 5,921,244 | A | | 7/1999 | Chen et al. |
| 2002/0133225 | A1 | | 9/2002 | Gordon |
| 2003/0175492 | A1 | * | 9/2003 | Dames et al. ............ 428/304.4 |
| 2006/0041182 | A1 | * | 2/2006 | Forbes et al. .................. 600/12 |

OTHER PUBLICATIONS

Florian Krotz, Cor De Wit, Hae-Young Sohn, Stefan Zahler, Torsten Gloe, Ulrich Pohl and Christian Plank, Magnetofection—A Highly Efficient Tool for Antisense Oligonucleotide Delivery in Vitro and In Vivo, May 2003, Molecular Therapy, vol. 7, pp. 700-710, No. 5, The American Society of Gene Therapy.

M. Laird Forrest, James T. Koerber, and Daniel W. Pack, A Degradable Polyethylenimine Derivative with Low Toxicity for Highly Efficient Gene Delivery, Bioconjugate Chem., 2003, pp. 934-940, vol. 14, American Chemical Society.

Michael A. Gosselin, Wenjin Guo, and Robert J. Lee, Efficient Gene Transfer Using. Reversibly Cross-Linked Low Molecular Weight Polyethylenimine, Bioconjugate Chem., 2001, pp. 989-994, vol. 12, American Chemical Society.

J. L. Arias, V. Gallardo, S. A. Gomez-Lopera, R. C. Plaza, and A. V. Delgado, Synthesis and Characterization of Poly(ethyl-2-cyanoacrylate) Nanoparticles with a Magnetic Core, Oct. 10, 2001, pp. 309-321, vol. 77, Journal of Controlled Release, Elsevier Science B.V.

S. A. Gomez-Lopera, R. C. Plaza, and A. V. Delgado, Synthesis and Characterization of Spherical Magnetite/Biodegradable Polymer Composite Particles, 2001, pp. 40-47, vol. 240, Journal of Colloid and Interface Science, Academic Press.

M. Igartua, P. Saulnier, B. Heurtault, B. Pech, J. E. Proust, J. L. Pedraz, and J. P. Benoit, Development and Characterization of Solid Lipid Nanoparticles Loaded with Magnetite, 2002, pp. 149-157, vol. 233, International Journal of Pharmaceutics, Elsevier Science B.V.

R. H. Muller, S. Maaben, H. Weyhers, F. Specht, and J. S. Lucks, Cytotoxicity of Magnetite-Loaded Polylactide, polylactide/Glycolide Particles and Solid Lipid Nanoparticles, 1996, pp. 85-94, vol. 138, International Journal of Pharmaceutics, Elsevier Science B.V.

Ernst Wagner, Kurt Zatloukal, Matt Cotton, Helen Kirlappos, Karl Machtler, David T. Curiel, and Max L. Birnstiel, Jul. 1992, pp. 6099-6103, vol. 89, Proc. Natl. Acad. Sci., USA.

Christian Plank, Franz Scherer, Ulrike Schillinger, Christian Bergemann, and Martina Anton, Magnetofection: Enhancing and Targeting Gene Delivery with Superparamagnetic Nanoparticles and Magnetic Fields, 2003, pp. 29-32, vol. 13, No. 1, Journal of Liposome Research, Marcel Dekker, Inc.

F. Scherer, M. Anton, U. Schillinger, J. Henke, C. Bergemann, A. Kruger, B. Gansbacher, and C. Plank, Magnetofection: enhancing and targeting gene delivery by magnetic force in vitro and in vivo, 2002, pp. 102-109, vol. 9, Gene Therapy, Nature Publishing Group.

Florian Krotz, Hae-Young Sohn, Torsten Gloe, Christian Plank, and Ulrich Pohl, Magnetofection Potentiates Gene Delivery to Culture Endothelial Cells, 2003, pp. 425-434, vol. 40, S. Karger AG, Basel.

M. De Cuyper, and M. Joniau, Magnetoliposomes Formation and Structural Characterizations, 1988, pp. 311-319, European Biophysics Journal, Springer-Verlag.

Sanaa E. Khalafalla, Magnetic Fluid, Chemtech, Sep. 1975, pp. 540-546.

Majeti N. V. Ravi Kumar, Nano and Microparticles as Controlled Drug Delivery Devices, 2000, pp. 234-258, vol. 3, No. 2, J Pharm Pharmaceut Sci.

David Quintanar-Guerrero, Eric Allemann, Hatem Fessi, and Eric Doelker, 1998, pp. 1113-1128, vol. 24, No. 12, Drug Development of Industrial Pharmacy, Marcel Dekker, Inc.

Isabelle Messai, Severine Munier, Yasemin Ataman-Onal, Bernard Verrier, and Thierry Delair, Elaboration of Poly(ethyleneimine) Coated Poly(D,L-lactic acid) Particles. Effect of Ionic Strength on the Surface Properties and DNA Binding Capabilities, 2003, pp. 293-305, vol. 32, Colloids and Surfaces B: Biointerfaces, Elsevier B.V.

Taeghwan Hyeon, Chemical Synthesis of Magnetic Nanoparticles, 2003, pp. 927-934, Chem Comm, The Royal Society of Chemistry.

MM OW Sullivan, JJ Green, and TM Przybycien, Development of a Novel Gene Delivery Scaffold Utilizing Colloidal Gold-Polyethylenimine Conjugates for DNA Condensation, 2003, pp. 1882-1890, vol. 10, Gene Therapy, Nature Publishing Group.

Ritsuko Ito, Yoshiharu Machida, Takanori Sannan, and Tsuneji Nagai, Magnetic Granules: a novel system for specific drug delivery to esophageal mucosa in oral administration, 1990, pp. 109-117, vol. 61, International Journal of Pharmaceutics, Elsevier Science Publishers B.V. (Biomedical Division).

Christian Plank, Martina Anton, Carsten Rudolph, Joseph Rosnecker & Florian Krotz, Enhancing and targeting nucleic acid delivery by magnetic force, 2003, pp. 745-758, vol. 3, No. 5, Expert Opinion Biol. Ther., Ashley Publications Ltd.

Zachary G. Forbes, Benjamin B. Yellen, Kenneth A. Barbee, and Gary Friedman, An Approach to Targeted Drug Delivery Based on Uniform Magnetic Fields, Sep. 2003, pp. 3372-3377, vol. 39, No. 5, IEEE Transactions on Magnetics.

Janet Fricker, Drug-eluting stents: flashy future or flash-in-the-pan?, Nov. 2001, pp. 1135-1137, vol. 6, No. 22, Drug Discovery Today, Elsevier Science Ltd.

Samer M. Garas, Philip Huber, and Neal A. Scott, Overview of therapies for prevention of restenosis after coronary interventions, 2001, pp. 165-178, vol. 92, Pharmacology & Therapeutics, Elsevier Science Inc.

A. H. Gershlick, Treating atherosclerosis: local drug delivery from laboratory studies to clinical trials, 2002, pp. 259-271, vol. 160, Atherosclerosis, Elsevier Science Ireland, Ltd.

Scott Goodwin, Caryn Peterson, Carl Hoh, and Craig Bittner, Targeting and retention of magnetic targeted carriers (MTCs) enhancing intra-arterial chemotherapy, 1999, pp. 132-139, vol. 194, Journal of magnetism and Magnetic Materials, Elsevier Science B.V.

Christoph Hehrlein, Amina Arab, and Christoph Bode, Drug-eluting stent: the "magic bullet" for prevention of restenosis?, 2002, pp. 417-423, vol. 97, No. 6, Basic Research in Cardiology, Steinkopff Verlag.

Hugh Herr, PhD, Presentation highlights: Prosthetic and orthotic limbs, May/Jun. 2002, pp. 11-12, vol. 39, No. 3, Journal of Rehabilitation Research and Development, VA/NIH Prosthetics Roundtable, http://www.vard.org/jour/02/39/3/sup/herr.htm.

Jing Liu, George Anthony Flores, and Rongsheng Sheng, In-vitro investigation of blood embolization in cancer treatment using magnetorheological fluids, 2001, pp. 209-217, vol. 225, Journal of Magnetism and Magnetic Materials, Elsevier Science B.V.

E. Regar, G. Sianos, and P. W. Serruys, Stent development and local drug delivery, 2001, pp. 227-248, vol. 59, British Medical Bulletin, The British Council.

Robert S. Schwartz, Elazer R. Edelman, Andrew Carter, Nicolas Chronos, Campbell Rogers, Keith A. Robinson, Ron Waksman, Judah Weinberger, Robert L. Wilensky, Donald N. Jensen, Bram D. Zuckerman, Renu Virmani and for the Consensus Committee, Drug-Eluting Stents in Preclinical Studies: Recommended Evaluation From a Consensus Group, 2002, pp. 1867-1873, vol. 106, Circulation: Journal of the American Heart Association, American Heart Association.

G. Segre and A. Silberberg, Behaviour of macroscopic rigid spheres in Poiseuille flow, 1962, pp. 115-157, vol. 14, Journal of Fluid Mechanics Digital Archive, Cambridge University Press.

R. Sheng, G. A. Flores, and J. Liu, In vitro investigation of a novel cancer therapeutic method using embolizing properties of magnetorheological fluids, 1999, pp. 167-175, vol. 194, Journal of magnetism and Magnetic Materials, Elsevier Science B.V.

International Search Report for PCT/US04/11861; Completed Jan. 10, 2005; Mailed Feb. 14, 2005.

\* cited by examiner

1. Iron oxide nanodispersion in chloroform

2. PLA NP formation

MAGNETICALLY-DRIVEN BIODEGRADABLE GENE DELIVERY NANOPARTICLES FORMULATED WITH SURFACE-ATTACHED POLYCATIONIC COMPLEX

BACKGROUND OF THE INVENTION

1. Field of Invention

This invention relates to delivery of biomaterial to a cell or a tissue, and more particularly it relates to delivery of biomaterial associated with particles.

2. Description of Related Art

In general, nanoparticles have been very ineffective vehicles for gene delivery, with expression levels below those seen with naked DNA. Thus, there has been relatively little progress with DNA incorporation into biodegradable sustained release particles. Also, problems encountered in gene therapy include slow accumulation and low concentration of gene vector in target tissues.

Nanoparticles formed from biodegradable polymers have been used to carry active molecules to sites in the body where the therapeutic effect is required (see Quintanar-Guerrero et al., Preparation techniques and mechanisms of formation of biodegradable nanoparticles from preformed polymers. Drug Dev Ind Pharm 1998; 24:1113-28; and Kumar MNR. Nano and microparticles as controlled drug delivery devices. J Pharm Pharmaceut Sci 2000; 3:234-58). Quintanar-Guerrero et al. describe various techniques available to prepare biodegradable nanoparticles from polymers such as for example, emulsification-solvent evaporation, solvent displacement, salting-out, and emulsification diffusion. In general, such nanoparticles have limited loading capacity for most hydrophilic drugs and also are not efficient in cases where rapid accumulation of active molecules is required at their target sites.

Various studies were conducted to improve delivery of a biomaterial such as viruses (e.g., adenovirus) and plasmid DNA by physical means such as an application of a magnetic field to a vector including magnetically responsive solid phases, which are micro-to nanometer sized particles or aggregates thereof (see Plank et al., Enhancing and targeting nucleic acid delivery by magnetic force. Expert Opin Biol Ther. 2003; 3:745-58 (Plank I thereafter); Plank et al., The magnetofection method: using magnetic force to enhance gene delivery. Biol. Chem. 2003; 384:737-47 (Plank II thereafter); Scherer et al. Magnetofection: enhancing and targeting gene delivery by magnetic force in vitro and in vivo. Gene Ther. 2002; 9:102-9).

Ito et al. describe application of magnetic granules (0.1-0.5 microns) as carriers for anti-cancer drugs administered orally in local targeting chemotherapy of esophageal cancer (see Magnetic Granules: A Novel System for Specific Drug Delivery to Esophageal Mucosa in Oral Administration. Int'l. J. of Pharmaceutics, 61 (1990), pp. 109-117). Compositions described by Ito et al. were not made as colloidal particles, and magnetic granules used therein were not stabilized.

U.S. Pat. No. 5,916,539 to Pilgrimm describes superparamagnetic particles useful in medicine for destroying tumors, increasing immunity and diagnosing conditions. The patent describes aggregates of superparamagnetic single-domain particles bearing on its surface chemically bound organic substances for further binding of active substances such as antigens, antibodies, haptens, protein A, protein G, endotoxin-binding proteis, lectins, and selectins.

Arias et al. describes an anionic polymerization procedure for preparing colloidal nanoparticles consisting of a magnetic core and a biodegradable polymeric shell wherein the polymerization medium was magnetite suspension in HCl solution (see Synthesis and Characterization of Poly(ethyl-2-cyanoacrylate) Nanoparticles with a Magnetic Core. J of Controlled Release 77 (2001), pp. 309-321).

Gómez-Lopera et al. describe preparation of colloidal particles formed by a magnetite nucleus and a biodegradable poly(DL-lactide) polymer coating by a double emulsion method, wherein aqueous suspension of magnetite particles was used to prepare an emulsion with the polymer (see Synthesis and Characterization of Spherical Magnetite/Biodegradable Polymer Composite Particles. J. of Colloid and Interface Science 240, 40-47 (2001)). It is significant that the magnetite in the cited studies was not incorporated as an organic suspension, resulting in its poor incorporation in the particle.

Plank et al. describe superparamagnetic iron oxide nanoparticles manufactured with polyelectrolyte surface coatings such as poly(ehylenimine) (PEI) and polylysine further associated with gene vectors by salt induced colloid aggregation (Magnetofection: enhancing and targeting gene delivery with superparamagnetic nanoparticles and magnetic fields. J Liposome Res. 2003; 13:29-32 (Plank III thereafter)). (See also Plank II, Scherer et al., Magnetofection: enhancing and targeting gene delivery by magnetic force in vitro and in vivo. Gene Ther. 2002; 9:102-9).

The same research group further used magnetic beads in combination with PEI and pDNA as a model of a non-viral vector mediated gene expression system for transfection of cells (see Krotz et al., Magnetofection potentiates gene delivery to cultured endothelial cells. J Vasc Res. 2003; 40(5):425-434) and delivery of antisense oligonucleotides in a catheter-based coronary angioplastic therapy for occlusive cardiovascular disease (see Krotz et al., Magnetofection-A highly efficient tool for antisense oligonucleotide delivery in vitro and in vivo. Mol Ther. 2003; 7:700-10). The magnetic beads used by this research group lack the concept of sustained release and increased colloidal stability achievable with biodegradable polymer-based particles. Moreover, the reported results show a considerable extent of cell toxicity caused by nanoparticulate formulations (see Plank II, supra). The PEI coating stability and a possible aggregation in biological fluids have not been examined, but might potentially be a concern in these formulations.

Müller et al. studied cytotoxicity of poly(lactide), poly(lactide-co-glucolide), poly(styrene) and solid lipid particles loaded with magnetite. No attempts to incorporate magnetite as a stable organic dispersion were described (see Cytotoxicity of Magnetite-Loaded Polylactide, Polylactide/Glycolide Particles and Solid Lipid Nanoparticles. Int'l. J. of Pharmaceutics 138 (1996) 85-94). Further, the possibility of loading the particles with a drug has not been examined.

Igartua et al. describe encapsulation of magnetite particles stabilized by oleic acid in solid lipid nanoparticles (see Development and Characterization of Solid Lipid Nanoparticles Loaded with Magnetite. Int'l. J. of Pharmaceutics 233 (2002) 149-157). The authors did not address using polymer as a matrix and presented no results on drug loading in such particles.

De Cuyper et al. describe magnetoliposomes which are phospholipid bilayer coated magnetite particles prepared by adsorption of sonicated phospholipids onto magnetite stabilized by lauric acid in an aqueous solution (see Magnetoliposomes. Formation and structural characterization. Eur Biophys J 1988; 15:311-319). Such liposomes are too small to be effectively manipulated by magnetic field. Although, ability to bind drug have not been studied, the liposomes prepared by this method have limited capacity for drug substances since they can be loaded only by surface adsorption.

Messai et al. describe poly (lactic acid)-based particles ((PLA nanoparticles) surface modified by electrostatic adsorption of PEI, wherein PEI is associated with DNA (see Elaboration of Poly(ethyleneimine) Coated Poly(D, L-lactic acid) Particles. Effect of Ionic Strength on the Surface Properties and DNA Binding Capabilities. Colloids and Surfaces B: Biointerfaces 32 (2003), pp. 293-305). PEI adsorbed onto PLA nanoparticles does not provide a stable coating and readily dissociates into the external medium upon dilution.

Sullivan et al. describe gene delivery scaffolds based on DNA plasmid condensation with colloidal gold/PEI conjugates (see Development of a Novel Gene Delivery Scaffold Utilizing Colloidal Gold-Polyethylenimine Conjugates for DNA Condensation. Gene Therapy (2003) 10, 1882-1890). Although, such conjugates when used as a vehicle for gene delivery exhibit improved size stability when compared to PEI alone, they cannot be targeted by magnetic field and lack sustained release properties.

Despite the foregoing developments, there is a need in the art for alternative means of delivery of biomaterial.

All references cited herein are incorporated herein by reference in their entireties.

BRIEF SUMMARY OF THE INVENTION

Accordingly, the invention provides a particle comprising a matrix-forming agent; and a polyelectrolyte-amphiphilic agent adduct wherein the polyelectrolyte-amphiphilic agent adduct is in physical communication with the matrix-forming agent.

In certain embodiments, the polyelectrolyte-amphiphilic agent adduct has a $C_4$-$C_{24}$ hydrocarbon chain. Preferably, the polyelectrolyte-amphiphilic agent adduct is poly(ethyleneimine) carboxylate. In certain embodiments, the polyelectrolyte-amphiphilic agent adduct is formed by an association of a polyelectrolyte with a first amphiphilic agent.

In certain embodiments, the particle further comprises a coated magnetic field-responsive agent having a magnetic field-responsive agent in communication with a second amphiphilic agent, wherein the coated magnetic field-responsive agent is in communication with the matrix-forming agent. In one variant, the first amphiphilic agent and the second amphiphilic agent are the same substance.

In certain embodiments, the particle further comprises a biomaterial in communication with at least one of the polyelectrolyte-amphiphilic agent adduct or the matrix-forming agent. In certain embodiments, the particle further comprises a biomaterial in communication with at least one of the polyelectrolyte-amphiphilic agent adduct or the matrix-forming agent, wherein the particle is free of the magnetic field-responsive agent.

In certain embodiments, the particle further comprises a stabilizer.

Further provided is a magnetic particle comprising a matrix-forming polymer; and a coated magnetic field-responsive agent comprising a magnetic field-responsive agent and a second amphiphilic agent, wherein the coated magnetic field-responsive agent is in communication with the matrix-forming polymer, provided that the magnetic particle is free of a polyelectrolyte. In certain embodiments, the magnetic particle further comprises a biomaterial in communication with the matrix-forming polymer.

Further provided is a particle comprising a matrix-forming polymer, a polyelectrolyte-amphiphilic agent adduct comprising a first $C_{12}$-$C_{24}$ carboxylate group, wherein the first $C_{12}$-$C_{24}$ carboxylate group is in physical communication with the matrix-forming polymer; a second amphiphilic agent comprising a second $C_{12}$-$C_{24}$ carboxylate group in communication with the matrix-forming polymer; and a magnetic-field responsive agent in communication with a second $C_{12}$-$C_{24}$ carboxylate group. In certain embodiments, the particle further comprises a stabilizer. In certain embodiments, the particle further comprises a biomaterial in communication with the polyelectrolyte-amphiphilic agent adduct and optionally with the matrix-forming polymer.

Further provided is a method of making the particle of the invention, the method comprising:
providing the matrix-forming agent;
providing a polyelectrolyte;
providing a first amphiphilic agent;
providing a first medium and a second medium;
optionally providing a stabilizer;
mixing at least the matrix-forming agent, the first medium, and the second medium and optionally the polyelectrolyte, the first amphiphilic agent, and/or the stabilizer to give a first mixture;
emulsifying the first mixture to give a first emulsion; and
removing the first medium and thereby forming the particle, on a condition that the polyelectrolyte, the first amphiphilic agent, and the stabilizer are provided to at least one of the first medium, the second medium, the first mixture, the first emulsion, or the particle such that the polyelectrolyte and the first amphiphilic agent form the polyelectrolyte-amphiphilic agent adduct. In certain embodiments, the method further comprises providing a biomaterial.

In another embodiment, the method further comprises providing a coated magnetic field-responsive agent to at least one of the first medium, the second medium, and/or the first mixture.

In one variant of this embodiment, the method further comprises providing a biomaterial, wherein the biomaterial is provided to at least one of the first mixture, the first emulsion and/or the particle.

Further provided is a method of making the magnetic particle of the invention, the method comprising:
providing the matrix-forming polymer;
providing the coated magnetic field-responsive agent;
providing a first medium and a second medium;
optionally providing a stabilizer;
mixing at least the matrix-forming polymer, the first medium, and the second medium to give a second mixture;
emulsifying the second mixture to give a second emulsion; and
removing the first medium and thereby forming the particle, on a condition that the coated magnetic field-responsive agent and optionally the stabilizer are provided to at least one of the first medium, the second medium, or the second mixture. One variant of this embodiment includes further providing a biomaterial. The biomaterial can be provided to at least one of the second mixture, the second emulsion or the magnetic particle.

Further provided is a method of making a particle, the method comprising:
providing a first medium and a second medium;
providing a coated magnetic field-responsive agent;
optionally providing a stabilizer;
providing a composition comprising a matrix-forming agent, a polyelectrolyte, a first amphiphilic agent and optionally the stabilizer;
dispersing the coated magnetic field-responsive agent in the first medium to form a dispersion;
mixing the composition with the dispersion;

adding the second medium to the composition and the dispersion to form a first mixture;

emulsifying the first mixture to give a first emulsion; and removing the first medium and thereby forming the particle.

Also provided is a particle made by the above method. In one variant, the particle further comprises a biomaterial.

Also provided is a method of delivery of a biomaterial to a target cell or a target tissue, the method comprising:

administering the particle of the invention comprising the matrix-forming agent, polyelectrolyte-amphiphilic agent adduct, the coated magnetic field-responsive agent and the biomaterial;

optionally providing a magnetic device associated with the target cell or the target tissue;

applying a magnetic force to the particle; and guiding the particle by the magnetic force and thereby delivering the biomaterial to the target cell or the target tissue.

Further provided is a method of delivery of a biomaterial to a target cell or a target tissue, the method comprising:

administering the particle of the invention comprising the matrix-forming agent, the coated magnetic field-responsive agent, and the biomaterial, wherein the particle is free of the polyelectrolyte;

optionally providing a magnetic device associated with the target cell or the target tissue;

applying a magnetic force to the particle; and guiding the particle toward the magnetic device by the magnetic force and thereby delivering the biomaterial to the target cell or the target tissue.

Also provided is a method of delivery of a biomaterial to a cell or a tissue, the method comprising:

administering the particle of the invention comprising the matrix-forming agent, the polyelectrolyte-amphiphilic agent adduct, and the biomaterial, wherein the particle is free of the magnetic field-responsive agent;

delivering the biomaterial to the cell or tissue using the particle as a carrier, wherein the cell is optionally contacted with a transfection agent prior to said delivering.

The particles of the present invention have the following features:

1. adjustable particle size and rapid cellular uptake;
2. surface or bulk binding of a biomaterial (e.g., DNA vectors);
3. biodegradable polymer matrix of the carrier;
4. the use of a polyelectrolyte (e.g., poly(ethyleneimine) (PEI)) for enhanced biomaterial delivery and protection, wherein the polyelectrolyte is complexed with or adducted to an amphiphilic agent;
5. optional co-incorporation of a magnetic field-responsive agent in association with an amphiphilic agent to confer a magnetic targeting capability to particles; and
6. optional inclusion of biocompatible surface-modifying agents to provide improved colloidal stability and "stealth" properties in vivo.

BRIEF DESCRIPTION OF SEVERAL VIEWS OF THE DRAWINGS

The invention will be described in conjunction with the following drawings in which like reference numerals designate like elements and wherein:

FIGS. 5A and 5B are bar graphs showing transfection efficacy of nanoparticles prepared as in Example 1 below and associated with green fluorescent protein encoding DNA at different theoretical charge ratios (5+/−, 10+/−, and 15+/−). The results are shown in comparison with PEI alone and PEI admixed to non-magnetic PLA nanoparticles prepared omitting stabilized magnetite incorporation and taken in amount corresponding to that of the magnetic nanoparticles. The transfection efficacy in the experimental and control groups was examined as a function of magnetic field exposure, wherein FIG. 5A depicts results obtained without magnetic field exposure and FIG. 5B depicts results obtained with magnetic field exposure.

DETAILED DESCRIPTION OF THE INVENTION

Figure 1A:
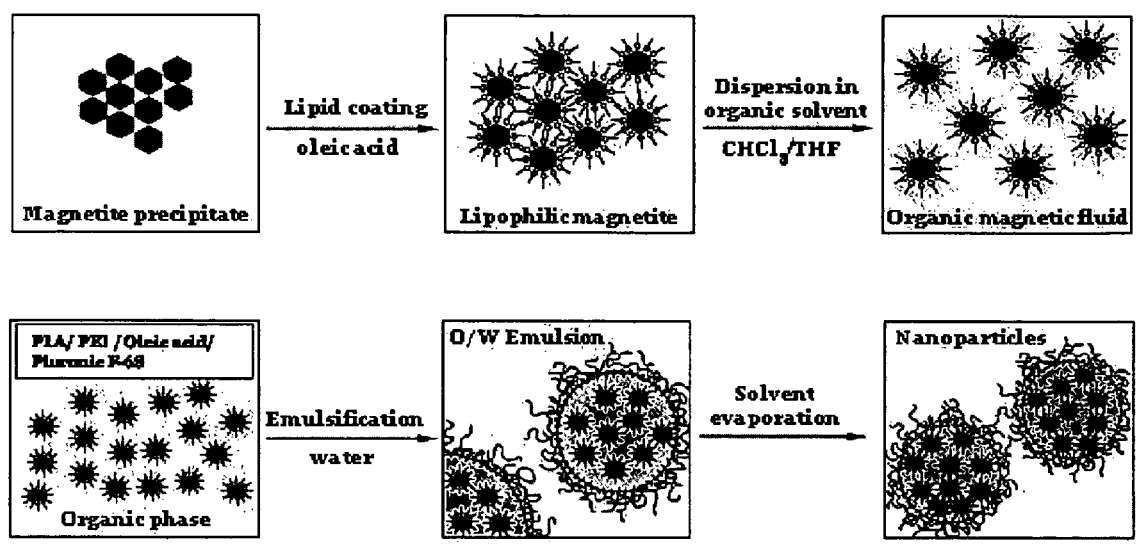
FIGS. 1A and 1B are schemes showing a preferred method of making the particle of the invention comprising the matrix-forming agent, polyelectrolyte-amphiphilic agent adduct, the coated magnetic field-responsive agent.

The invention was driven by the desire to develop particles capable of carrying and delivering biomaterial. In certain embodiments, the particles are capable of targeted delivery of biomaterial under influence of a magnetic force, wherein the particles further comprise a coated magnetic field-responsive agent.

Accordingly, the invention provides a particle comprising a matrix-forming agent and a polyelectrolyte-amphiphilic agent adduct, wherein the polyelectrolyte-amphiphilic agent adduct is in physical communication with the matrix-forming agent. In certain embodiments, the particle further comprises a biomaterial in communication with at least one of the polyelectrolyte-amphiphilic agent adduct or the matrix-forming agent.

Advantageously, the particle of the invention has two compartments for incorporation of a biomaterial: the polyelectrolyte and the matrix-forming agent, wherein one of the compartments or both can be utilized. The particles of the invention provide an improved loading of a biomaterial such as, for example, a plasmid DNA, by utilizing an ionic binding with a polyelectrolyte (e.g., poly(ethyleneimine) (PEI)) complexed with or adducted to an amphiphilic agent to form a polyelectrolyte-amphiphilic agent adduct. The polyelectrolyte-amphiphilic agent adduct has a strong association with the surface of particles due to a lipophilic and hydrophilic domains with high affinities to respective media used in the emulsification step of the particle preparation. The polyelectrolyte useful in this invention can be cationic (e.g., PEI) or anionic (e.g., dextran sulfate).

A non-limiting example of the particle comprising an anionic polyelectrolyte is PLA (the matrix-forming polymer)/stearylamine (the amphiphilic agent)/dextran sulfate (polyanion)/PDGF (cationic biomaterial). A non-limiting example of the particle comprising a cationic polyelectrolyte is PLA/oleic acid (the amphiphilic agent)/PEI (the amphiphilic agent)/DNA (anionic biomaterial).

In addition, the biomaterial can be incorporated in the particles of the invention by being adsorbed, entangled with or entrapped by the matrix-forming polymer.

In certain embodiments, the particles of the invention have magnetic targeting capabilities and thus enable the enhanced targeted delivery of the biomaterial to specific cells or organs either in cell culture or in vivo, wherein a magnetic field gradient is induced by a magnetic field. The particles of the invention interface well with, for example, a nanoscale controllable magnetic patterned device surface (the magnetic device) for binding, release, and repeated loading of drug/gene delivery systems. Thus, in certain embodiments, the particle further comprises a coated magnetic field-responsive agent having a magnetic field-responsive agent in communication with an amphiphilic agent, wherein the coated magnetic field-responsive agent is in communication with the matrix-forming agent. In certain embodiments, such particle further comprises a biomaterial in communication with at least one of the polyelectrolyte-amphiphilic agent adduct or the matrix-forming agent.

In certain embodiments, the particle of the invention comprises a matrix-forming polymer, a polyelectrolyte-amphiphilic agent adduct comprising a first $C_{12}$-$C_{24}$ carboxylate group in physical communication with the matrix-forming polymer, a second amphiphilic agent comprising a second $C_{12}$-$C_{24}$ carboxylate group in communication with the matrix-forming polymer; and a magnetic-field responsive agent in communication with a second $C_{12}$-$C_{24}$ carboxylate group. In certain embodiments, the particle further comprises a stabilizer. In certain embodiments, the particle further comprises a biomaterial in communication with the polyelectrolyte-amphiphilic agent adduct and optionally, with the matrix-forming polymer.

In a preferred embodiment, the particle of the invention comprises poly(lactic acid) (PLA), PEI-oleic acid adduct, Pluronic F-68, magnetite coated with oleic acid (the coated magnetic field-responsive agent) and DNA, wherein PLA, PEI-oleic acid adduct, and Pluronic F-68 were premixed, then mixed with a dispersion of magnetite/oleic acid in an organic solvent, and emulsified in water, followed by removal of organic solvent.

Further, the particle of the invention can be a magnetic particle comprising a matrix-forming polymer; and a coated magnetic field-responsive agent comprising a magnetic field-responsive agent and a second amphiphilic agent, wherein the coated magnetic field-responsive agent is in communication with the matrix-forming polymer, provided that the magnetic particle is free of a polyelectrolyte. A used herein, the term "magnetic particle" denotes a particle possessing magnetic capabilities conferred by the coated magnetic field-responsive agent but in the absence of the polyelectrolyte to differentiate from a particle possessing magnetic capabilities and comprising the polyelectrolyte. In certain embodiments, the magnetic particle further comprises a biomaterial in communication with the matrix-forming polymer.

The particle of the invention can be used for delivery of biomaterial entrapped in or adsorbed on the matrix-forming polymer and/or associated with the particle surface via the polyelectrolyte for various applications such as, for example, drug therapy, chemotherapy, chemoembolization, hyperthermic cancer treatment, diagnostics, and radiotherapy.

One of the applications for this formulation is a targeted gene or drug delivery to the heart.

In one embodiment of the invention, a cardiac catheterization is carried out with positioning of a powerful magnet in the part of the heart where gene delivery is desired, for example, in the right atrium (a targeted tissue). Next, the particles of the invention (e.g., the biodegradable PEI-modified magnetic nanoparticles loaded with DNA) are administered to the coronary artery (e.g., by injection) and the myocardial circulation together with the magnetic field localizes the bulk of the particles in the desired area, the right atrial myocardium. A similar approach could be applied to virtually any target cell or organ region by providing the particles of the invention and a magnetic device associated with the targeted cell or the targeted tissue.

The particles of the invention can be used also for the prevention, diagnostic, or treatment of various conditions or disorders such as, for example, tumors, gastro-intestinal disease, pulmonary and bronchial disorders by delivering the appropriate biomaterial. The particles of the invention can also be used in hormonal therapy and anesthetic medication.

Also, the particles of the invention can be used as an analytical tool, for example for screening.

Delivery of biomaterial under influence of magnetic force includes reversible movement of particles from one target site to another.

In certain embodiments, the particle further comprises a biomaterial in communication with at least one of the polyelectrolyte-amphiphilic agent adduct or the matrix-forming agent, wherein the particle is free of the magnetic field-responsive agent.

The particle of the invention, its components, and methods of making the particle will be described in detail below.

Particle

Figure 1B:
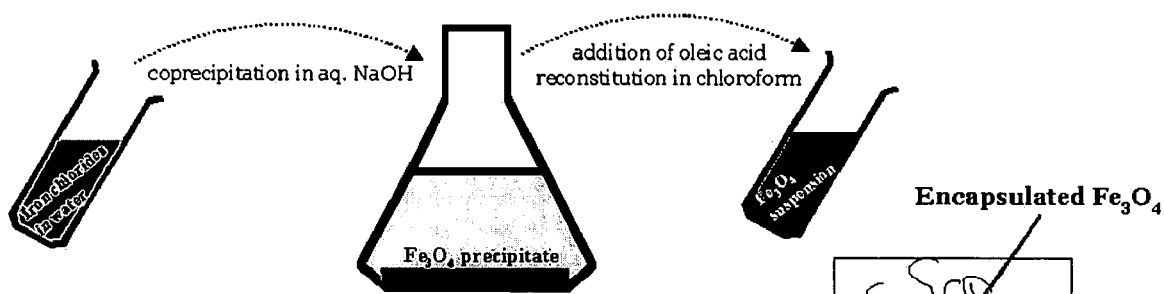
Figure 1B:
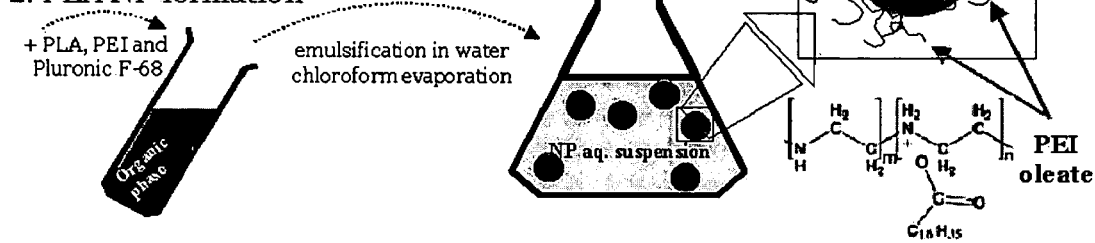
Figure 1C:
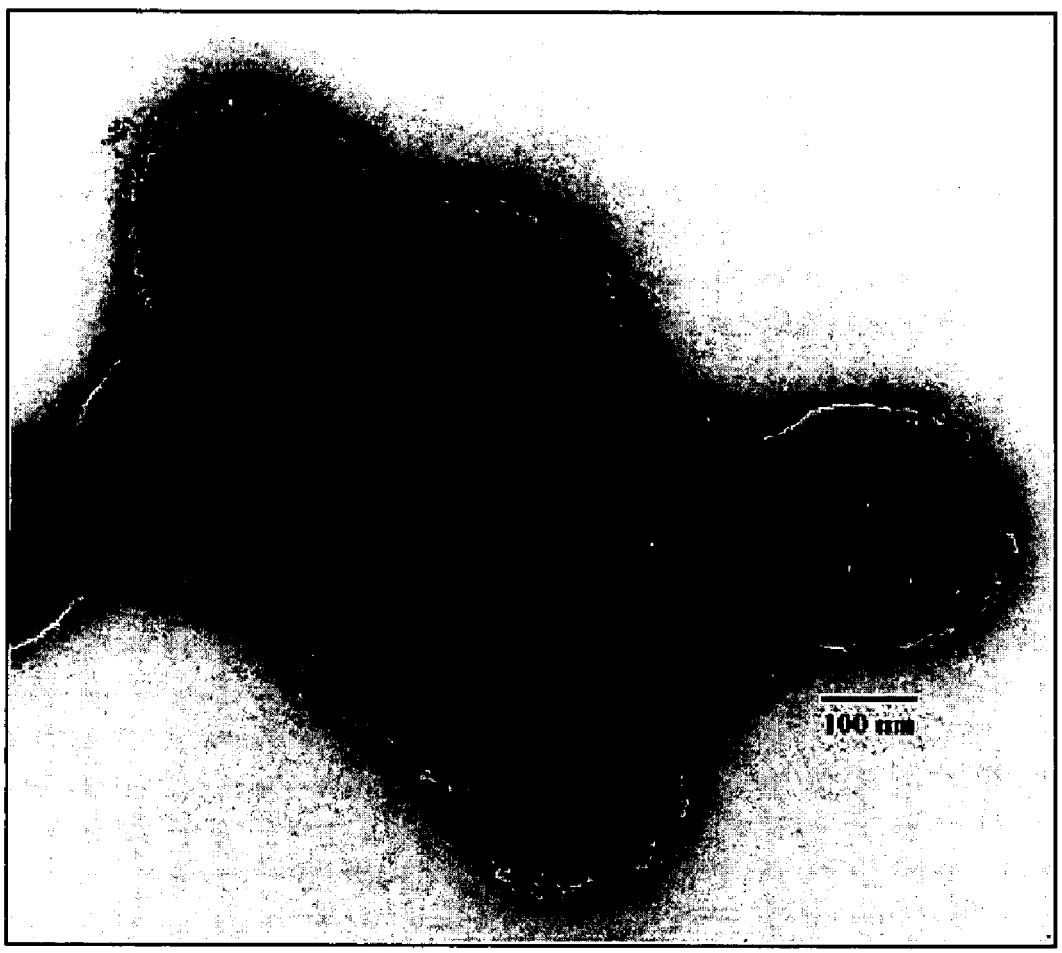
FIG. 1C is a transmission electron micrograph of nanoparticles containing magnetite.

The term "particle" as used herein denotes a solid colloidal particle having a diameter of about 5 nm to about 10 microns. The particle can be a sphere or a capsule, wherein the sphere is composed of a solid matrix, while the capsule has an oil-based or water-based core surrounded by the matrix-forming polymer. An example of a magnetic particle is shown in FIG. 1C. The particle can have one or more coated magnetic field-responsive agents incorporated within the matrix-forming polymer. Preferably, multiple coated magnetic nanocrystals are incorporated in the core of the particle.

Matrix-Forming Agent and Matrix-Forming Polymer

The matrix-forming agent used in the invention includes synthetic or natural polymers and non-polymeric substances.

The term "matrix-forming polymer" as used herein denotes a synthetic or a natural polymer, which forms the core of the particle. The matrix-forming polymer can be biodegradable, non-biodegradable, biocompatible, and is water-insoluble. The release kinetics of biomaterial from nanoparticles can be determined by the rate of the matrix-forming polymer's degradation, diffusion or dissolution of material entrapped in the particle or desorption of surface-bound substances.

Non-limiting examples of natural polymers are proteins, polysaccharides and lipids as described by Quintanar-Guerrero et al., supra and Kumar, supra. Non-limiting examples of synthetic polymers are poly(ester)s, poly(urethane)s, poly(alkylcyanoacrylate)s, poly(anhydride)s, poly(ethylenevinyl acetate), poly(lactone)s, poly(styrene)s, poly(amide)s, poly(acrylonitrile)s, poly(acrylate)s, poly(metacrylate)s, poly(orthoester)s, poly(ether-ester)s, poly(tetrafluoroethylene)s, mixtures thereof and copolymers of corresponding monomers. In certain embodiments, the poly(ester) is a member selected from the group consisting of poly(lactide), poly(glycolide), poly(lactide-co-glycolide), poly($\epsilon$-caprolactone), poly(dioxanone), poly(hydroxybutyrate), and poly(ethylene terephthalate).

Non-limiting examples of non-polymeric substances are solid lipids such as glycerides and fatty acids.

Amphiphilic Agent

The term "amphiphilic agent" as used herein denotes a biocompatible agent having a molecule comprising a reactive group and a lipophilic group. Non-limiting examples of amphiphilic agents are fatty acids and lipids as well as salts thereof such as carboxylates, phosphonates, bisphosphonates, phosphates, sulfonates, and sulfates. In certain embodiments, fatty acids are $C_{12}$-$C_{24}$ carboxylic acids and salts or esters thereof; the preferred fatty acid is oleic acid. In certain embodiments, lipids are phospholipids such as phosphatidylglycerol and phosphatidylinositol. Amphiphilic agent can also be cationic, such as stearylamine, 3$\beta$-(N-[dimethylamine ethane] carbamoyl) cholesterol (DC-Chol), N-[1-(2,3-dioleoyloxy)propyl]-N,N,N-trimethylammonium chloride (DOTAP).

One of the functions of the amphiphilic agent is to provide a connection between the matrix-forming agent and the polyelectrolyte. In this instance, the amphiphilic agent is referred to as "a first amphiphilic agent." An amphiphilic agent is also used for forming a coated magnetic field-responsive agent and is referred to as "a second amphiphilic agent". A first amphiphilic agent and a second amphiphilic agent can be the same or different.

The reactive group of the amphiphilic agent is a polar chemical group such as, for example, a carboxylate group, a phosphonate group, a bisphosphonate group, a phosphate group, a sulfonate group, and a sulfate group. The association between the amphiphilic agent and the polyelectrolyte may be ionic (e.g., an ammonium carboxylate ion-pair) or covalent (e.g. via amide, imine, urethane, urea, alkyl bond, etc.).

The lipophilic group of the amphiphilic agent is a hydrocarbon chain with low water affinity, preferably a $C_4$-$C_{24}$ chain having all saturated bonds (e.g., lauric acid and palmitic acid) or at least one unsaturated bond (e.g., oleic acid). The hydrocarbon chain can present a cyclic structure (e.g. cholesterol or cholic acid). The hydrocarbon chain can further have one or more hydrogen atoms substituted with for example an aromatic group. The hydrocarbon chain can further have one of more carbon atoms substituted with heteroatoms (e.g., nitrogen, sulfur, and oxygen).

The adduct of the amphiphilic agent and the polyelectrolyte can be preformed or made in situ in the course of the particle preparation.

Polyelectrolyte

The polyelectrolyte of the invention provides a connection between the matrix-forming polymer and the biomaterial, wherein the polyelectrolyte is associated with the matrix-forming polymer through the amphiphilic agent. The polyelectrolyte can be cationic or anionic.

In one embodiment, the polyelectrolyte and the biomaterial are ionically associated. For example, the polyelectrolyte is cationic (e.g., poly(ethyleneimine)) and the biomaterial is anionic (e.g., DNA) or the polyelectrolyte is anionic (e.g., dextran sulfate) and the biomaterial is cationic (e.g., PDGF).

Association between the biomaterial and the polyelectrolyte-amphiphilic agent adduct can also be covalent, wherein reactive groups of the biomaterial chemically react with reactive groups of the polyelectrolyte-amphiphilic agent.

In certain embodiments, the polyelectrolyte is a polycation. Non-limiting examples of polycations include poly(ethyleneimine), poly(allylamine), poly(lysine), poly(arginine), poly(spermine), poly(spermidine), poly(propyleneimine), poly(N-ethyl-4-vinyl pyridinium bromide), polyamidoamine dendrimer and derivatives thereof.

Preferably, PEI used in the invention has a molecular weight of about 25 KDa, and more preferably about 14 KDa or less to enhance its elimination from the body or is a biodegradable derivative thereof.

PEI with the molecular weight of at least 25 KDa is known to be toxic to cells. Decreasing the size of PEI reduces the toxicity but it also reduces the efficacy of gene transfer (see Forrest et al., Gosselin et al.).

Examples of biodegradable PEI derivatives useful in the invention can be found in Gosselin et al., Efficient gene transfer using reversibly cross-linked low molecular weight polyethylenimine, Bioconjug Chem. 2001 November-December; 12(6):989-94, and are expected to be less toxic. PEI derivatives can be prepared by cross-linking 800 Da PEI with dithiobis(succinimidylpropionate) (DSP) and/or dimethyl 3,3'-dithiobispropionimidate 2HCl (DTBP).

Forrest et al., A degradable polyethylenimine derivative with low toxicity for highly efficient gene delivery, Bioconjug Chem. 2003 September-October; 14(5):934-40) disclose highly branched 14-30 KDa polycations that are biodegradable analogs of PEI (25 KDa) produced by addition of amino groups on 800 Da PEI to diacrylates such as, for example, 1,3-butanediol diacrylate of varying spacer length. These or similar derivatives can also be useful in the invention.

Magnetic Field-Responsive Agent

A magnetic field-responsive agent as used herein is a paramagnetic, superparamagnetic, or ferromagnetic substance capable of moving under influence of a magnetic force. In certain embodiments, the magnetic field-responsive agent is a member selected from the group consisting of iron, cobalt or nickel, alloys thereof, oxides thereof and mixed oxides/hydroxides of Fe(II) and/or Fe(III) with at least one of Co(II), Mn(II), Cu(II), Ni(II), Cr(III), Gd(III), Dy(III), and Sm(III). Preferably, the magnetic field-responsive agent is at least one of $Fe_3O_4$, gamma-$Fe_2O_3$, or a mixture thereof. Preferably, the magnetic field-responsive agent is iron oxide in a shape of nanocrystals.

The magnetic field-responsive agent can be prepared by methods known in the art in various shapes and sizes (see Hyeon T., Chemical Synthesis of Magnetic Nanoparticles. The Royal Society of Chemistry 2003, Chem. Commun., 2003, 927-934). In certain embodiments, iron oxide nanocrystals were obtained by precipitation of mixed iron chlorides in the presence of a base in aqueous medium (see Khalafalla S E. Magnetic fluids, Chemtech 1975, September: 540-547).

The term "coated magnetic field-responsive agent" as used herein denotes a magnetic field-responsive agent in communication with an amphiphilic agent (an amphiphilic agent can be defined as "first" or "second" to indicate that these agents can be different substances, however embodiments in which these agents are the same are contemplated as well). In the particle of the invention, the coated magnetic field-responsive agent is in communication with the matrix-forming agent.

Stabilizing Agent

Optionally, the particle of the invention includes a stabilizing agent. Non-limiting examples of stabilizing agents include poly(sorbate) (e.g., TWEEN (Merck and Co. Inc., Whitehouse Station N.J., USA)), sorbitan ester, ethylene oxide-propylene oxide block copolymers (e.g., poloxamer), poloxamine, poly(ethylene glycol) (PEG), alkyl polyethylene glycol ether, PEG-based non-ionic surfactants (e.g., fatty acid polyethylene glycol ester and mixtures thereof). Examples of the functions of such stabilizing agents include providing steric protection, contributing to the stability in high ionic strength media in vitro and in serum in vivo, preventing rapid sequestration of the nanoparticles by the reticuloendothelial system following an intravenous injection.

Biomaterial

The biomaterial of the present invention can be any molecule or macromolecule having a therapeutical utility. In certain embodiments of the composition, the biomaterial is a member selected from the group consisting of a nucleic acid, a protein, a peptide, an oligonucleotide, an antibody, an antigen, a viral vector, a bioactive polypeptide, a polynucleotide coding for the bioactive polypeptide, a cell regulatory small molecule, a gene therapy agent, a gene transfection vector, a receptor, a cell, a drug, a drug delivering agent, an antimicrobial agent, an antibiotic, an antimitotic, an antisecretory agent, an anti-cancer chemotherapeutic agent, steroidal and non-steroidal anti-inflammatories, a hormone, a proteoglycan, a glycosaminoglycan, a free radical scavenger, an iron chelator, an antioxidant, an imaging agent, and a radiotherapeutic agent.

In certain embodiments of the composition, the biomaterial is any molecule or macromolecule to which a suitable ionizable reactive group, such as, for example, a carboxy (—COOH) group or an amino (—NH$_2$) group is attached.

The biomaterial can associate with the particle in several ways. In one embodiment, the biomaterial is in an ionic association with the charged groups of the polyelectrolyte-amphiphilic agent adduct (e.g., the carboxylate group) while the lipophilic part of the polyelectrolyte-amphiphilic agent adduct anchored in the matrix or chemically bound to the matrix-forming polymer of the particle. Association between the biomaterial and the polyelectrolyte-amphiphilic agent adduct can also be covalent, wherein reactive groups of the biomaterial chemically react with reactive groups of the polyelectrolyte-amphiphilic agent. Based on the desired type of the association, persons skilled in the art would be able to select biomaterials with reactive groups capable of interacting with the polyelectrolyte-amphiphilic agent adduct. A person skilled in the art would appreciate that such interactions would secure biomaterial predominantly to the outer surface of the particle.

In certain embodiments, the biomaterial can be in physical association (i.e., entrapped or adsorbed) with the matrix-forming polymer. Examples of entrapped biomaterial include Taxol (i.e., a substance soluble in an organic solvent).

Substances that are helpful to enhance bioavailability or stability of biomolecules, such as, for example, aurine, can also be entrapped as discussed above.

Combinations of biomaterial entrapped inside the particle and biomaterial attached to the outer surface of the particle (i.e., ionic or covalent bonding) are also contemplated. Same or different biomaterials can be used. For example, retinoid acid can have a dual function and can be used instead of an amphiphilic agent (e.g., oleic acid).

Suitable biomaterials include pharmaceuticals, nucleic acid sequences, such as transposons, signaling proteins that facilitate wound healing, such as TGF-β, FGF, PDGF, IGF and GH proteins that regulate cell survival and apoptosis, such as Bcl-1 family members and caspases; tumor suppressor proteins, such as the retinoblastoma, p53, PAC, DCC. NF1, NF2, RET, VHL and WT-1 gene products; extracellular matrix proteins, such as laminins, fibronectins and integrins; cell adhesion molecules such as cadherins, N-CAMs, selectins and immunoglobulins; anti-inflammatory proteins such as Thymosin beta-4, IL-10 and IL-12.

In certain embodiments, the biomaterial includes at least one of heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; a remodeling inhibitor; deoxyribonucleic acid, an antisense nucleotide or another agent for molecular genetic intervention; methotrexate or another antimetabolite or antiproliferative agent; tamoxifen citrate, Taxol™ or derivatives thereof, or other anti-cancer chemotherapeutic agents; dexamethasone, dexamethasone sodium phosphate, dexamethasone acetate or another dexamethasone derivative, or another anti-inflammatory steroid or a non-steroidal anti-inflammatory agent; cyclosporin or another immunosuppressive agent; trapidal (a PDGF antagonist), angiogenin, angiopeptin (a growth hormone antagonist), a growth factor or an anti-growth factor antibody, or another growth factor antagonist; dopamine, bromocriptine mesylate, pergolide mesylate or another dopamine agonist; radiotherapeutic agent; iodine-containing compounds, barium-containing compounds, gold, tantalum, platinum, tungsten or another heavy metal functioning as a radiopaque agent; a cellular component; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; a $^{14}$C—, $^3$H—, $^{32}$P- or $^{36}$S-radiolabelled form or other radiolabelled form of any of the foregoing; a hormone; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin or other antibody targeted therapy agents; gene therapy agents; and enalapril and other prodrugs, or a mixture of any of these.

Additionally, the biomaterial can be a component of any affinity-ligand pair. Examples of such affinity ligand pairs include avidin-biotin and IgG-protein A. Furthermore, the biomaterial can be either component of any receptor-ligand pair. One example is transferrin and its receptor. Other affinity ligand pairs include powerful hydrogen bonding or ionic bonding entities such as chemical complexes. Examples of the latter include metallo-amine complexes. Other such attractive complexes include nucleic acid base pairs, via immobilizing oligonucleotides of a specific sequence, especially antisense. Nucleic acid decoys or synthetic analogues can also be used as pairing agents to bind a designed gene vector with attractive sites. Furthermore, DNA binding proteins can also be considered as specific affinity agents; these include such entities as histones, transcription factors, and receptors such as the gluco-corticoid receptor.

In one preferred embodiment, the biomaterial is an anti-nucleic acid antibody. The antibody can therefore specifically bind a nucleic acid, which encodes a product (or the precursor of a product) that decreases cell proliferation or induces cell death, thereby mitigating the problem of restenosis in arteries and other vessels. The nucleic acid that is tethered to a support via the antibody can efficiently transfect/transducer cells. In general terms, the field of "gene therapy" involves delivering into target cells some polynucleotide, such as an antisense DNA or RNA, a ribozyme, a viral fragment, or a functionally active gene, that has a therapeutic or prophylactic effect on the cell or the organism containing it. The antibody of the composition can be a full-length (i.e., naturally occurring or formed by normal immuno-globulin gene fragment recombinatorial processes) immunoglobulin molecule (e.g., an IgG antibody, or IgM or any antibody subtype) or an immunologically active (i.e., specifically binding) portion of an immuno-globulin molecule. The antibody comprises one or more sites, which specifically bind with a nucleic acid (i.e., which does not substantially bind other types of molecules). The binding site can be one that binds specifically with a nucleic acid of a desired type without regard to the nucleotide sequence of the nucleic acid. The binding site can, alternatively, be one which binds specifically only with a nucleic acid comprising a desired nucleotide sequence.

The complex formed between a polynucleotide and a cognate antibody can be immobilized on a variety of surfaces such that, when the surface is exposed to a physiological environment in situ, the attached polynucleotide is released, over time, in a manner that enhances delivery of the polynucleotide to cells in the proximity. DNA transfer by way of immunospecific tethering has previously been shown to maintain the nucleic acid in regions that are subject to gene therapy.

Examples of suitable antibodies include Fv, F(ab), and F(ab')$_2$ fragments, which can be generated is conventional fashion, as by treating an antibody with pepsin or another proteolytic enzyme. The nucleic acid-binding antibody useful in the present invention can be polyclonal antibody or a monoclonal antibody. A "monoclonal" antibody comprises only one type of antigen binding site that specifically binds with the nucleic acid. A "polyclonal" antibody can comprise multiple antigen binding sites that specifically bind the nucleic acid. An antibody employed in this invention preferably is a full-length antibody or a fragment of an antibody, such as F(ab')$_2$, that possesses the desired binding properties.

A nucleic acid for use in the present invention can be any polynucleotide that one desires to transport to the interior of a cell. In this context, a "therapeutic polynucleotide" is a polymer comprised of nucleotides that, when provided to or expressed in a cell, alleviates, inhibits, or prevents a disease or adverse condition, such as inflammation and/or promotes tissue healing and repair (e.g., wound healing). The nucleic acid can be composed of deoxyribonucleosides or ribonucleosides, and can have phosphodiester linkages or modified linkages, such as those described below. The phrase "nucleic acid" also encompasses polynucleotides composed of bases other than the five that are typical of biological systems: adenine, guanine, thymine, cytosine and uracil.

A suitable nucleic acid can be DNA or RNA, linear or circular and can be single-or-double-stranded. The "DNA" category in this regard includes: cDNA; genomic DNA; triple helical, supercoiled, Z-DNA and other unusual forms of DNA; polynucleotide analogs; an expression construct that comprises a DNA segment coding for a protein, including a therapeutic protein; so-called "antisense" constructs that, upon transcription, yield a ribozyme or an antisense RNA; viral genome fragments, such as viral DNA; plasmids and cosmids; and a gene or gene fragment.

The nucleic acid also can be RNA, for example, antisense RNA, catalytic RNA, catalytic RNA/protein complex (i.e., a "ribozyme"), and expression construct comprised of RNA that can be translated directly, generating a protein, or that can be reverse transcribed and either transcribed or transcribed and then translated, generating an RNA or protein product, respectively; transcribable constructs comprising RNA that embodies the promoter/regulatory sequence(s) necessary for the generation of DNA by reverse transcription; viral RNA; and RNA that codes for a therapeutic protein, inter alia. A suitable nucleic acid can be selected on the basis of a known, anticipated, or expected biological activity that the nucleic acid will exhibit upon delivery to the interior of a target cell or its nucleus.

The length of the nucleic acid is not critical to the invention. The nucleic acid can be linear or circular double-stranded DNA molecule having a length from about 100 to 10,000 base pairs in length, although both longer and shorter nucleic acids can be used.

The nucleic acid can be a therapeutic agent, such as an antisense DNA molecule that inhibits mRNA translation. Alternatively, the nucleic acid can encode a therapeutic agent, such as a transcription or translation product which, when expressed by a target cell to which the nucleic acid-containing composition is delivered, has a therapeutic effect on the cell or on a host organism that includes the cell. Examples of therapeutic transcription products include proteins (e.g., antibodies, enzymes, receptors-binding ligands, wound-healing proteins, anti-restenotic proteins, anti-oncogenic proteins, and transcriptional or translational regulatory proteins), antisense RNA molecules, ribozymes, viral genome fragments, and the like. The nucleic acid likewise can encode a product that functions as a marker for cells that have been transformed, using the composition. Illustrative markers include proteins that have identifiable spectroscopic properties, such as green fluorescent protein (GFP) and proteins that are expressed on cell surfaces (i.e., can be detected by contacting the target cell with an agent which specifically binds the protein). Also, the nucleic acid can be a prophylactic agent useful in the prevention of disease.

A nucleic-acid category useful in the present invention encompasses polynucleotides that encode proteins that affect wound-healing. For example, the genes egf, tgf, kgf, hb-egf, pdgf, igf, fgf-1, fgf-2, vegf, other growth factors and their receptors, play a considerable role in wound repair.

Another category of polynucleotides, coding for factors that modulate or counteract inflammatory processes, also is useful for the present invention. Also relevant are genes that encode an anti-inflammatory agent such as MSH, a cytokine such as IL-10, or a receptor antagonist that diminishes the inflammatory response.

Suitable polynucleotides can code for an expression product that induces cell death or, alternatively, promotes cell survival, depending on the nucleic acid. These polynucleotides are useful not only for treating tumorigenic and other abnormal cells but also for inducing apoptosis in normal cells. Accordingly, another notable nucleic-acid category for the present invention relates to polynucleotides that, upon expression, encode an anti-oncogenic protein or, upon transcription, yield an anti-oncogenic antisense oligonucleotide. In this context, the phrases "anti-oncogenic protein" and "anti-oncogenic antisense oligonucleotide" respectively denote a protein or an antisense oligonucleotide that, when provided to any region where cell death is desired, or the site of a cancerous or precancerous lesion in a subject, prevents, inhibits, reverses abnormal and normal cellular growth at the site or induces apoptosis of cells. Delivery of such a polynucleotide to cells, pursuant to the present invention, can inhibit cellular growth, differentiation, or migration to prevent movement or unwanted expansion of tissue at or near the site of transfer. Illustrative of this anti-oncogenic category are polynucleotides that code for one of the known anti-oncogenic proteins. Such a polynucleotide would include, for example, a nucleotide sequence taken or derived from one or more of the following genes: abl, akt2, apc, bcl2-alpha, bcl2-beta, bcl3, bcl3, bcl-x, bad, bcr, brca1, brca2, cbl, ccndl, cdk4, crk-II, csflr/fins, dbl, dcc, dpc4/smad4, e-cad, e2fl/rbap, egfr/erbb-1, elk1, elk3, eph, erg, ets1, ets2, fer, fgr/src2, fos, fps/fes, fral, fra2, fyn, hck, hek, her2/erbb-2/neu, her3/erbb-3, her4/erbb-4, hras1, hst2, hstfl, ink4a, ink4b, int2fgf3, jun, junb, jund, kip2, kit, kras2a, kras2b, ck, lyn, mas, max, mcc, met, mlh1, mos, msh2, msh3, msh6, myb, myba, mybb, myc, mycll, mycn, nf1, nf2, nras, p53, pdgfb, pims1, pms1, pms2, ptc, pten, raft, rbl, rel, ret, ros1, ski, src1, tall, tgfbr2, thral, thrb, tiam1, trk, vav, vh1, waf1, wnt1, wnt2, wt1 and yes1 By the same token, oligonucleotides that inhibit expression of one of these genes can be used as anti-oncogenic antisense oligonucleotides.

Nucleic acids having modified inter-nucleoside linkages also can be used in composition according to the present invention. For example, nucleic acids can be employed that contain modified internucleoside linkages, which exhibit increased nuclease stability. Such polynuclotides include, for example, those that contain one or more phosphonate, phosphorothioate, phosphorodithioate, phosphoramidate methoxyethyl phosphoramidate, formacetal, thioformacetal, diisopropylsityl, acetamidate, carbamate, dimethylene-sulfide (—$CH_2$—S—$CH_2$—), dimethylene-sulfoxide (—$CH_2$—SO—$CH_2$—), dimethylenesulfone (—$CH_2$—$SO_2$—$CH_2$—), 2'-O-alkyl, and 2'-deoxy-2'-fluoro-phosphorothioate internucleoside linkages.

For present purposes, a nucleic acid can be prepared or isolated by any conventional means typically used to prepare or isolate nucleic acids. For example, DNA and RNA can be chemically synthesized using commercially available reagents and synthesizers by known methods. RNA molecules also can be produced in high yield via in vitro transcription techniques, using plasmids such as SP65, available from Promega Corporation (Madison, Wis.). The nucleic acid can be purified by any suitable means. For example, the nucleic acid can be purified by reverse-phase or ion exchange HPLC, size exclusion chromatography, or gel electrophoresis. Of course, the skilled artisan will recognize that the method of purification will depend in part on the size of the DNA to be purified. The nucleic acid also can be prepared via any of the innumerable recombinant techniques that are known or that are developed hereafter.

A suitable nucleic acid can be engineered into a variety of known host vector systems that provide for replication of the nucleic acid on a scale suitable for the preparation of an inventive composition.

Vector systems useful in the present invention can be viral or non-viral. Particular examples of viral vector systems include adenovirus, retrovirus, adeno-associated virus and herpes simplex virus. Preferably, an adenovirus vector is used. A non-viral vector system includes a plasmid, a circular, double-stranded DNA molecule. Viral and nonviral vector systems can be designed, using known methods, to contain the elements necessary for directing transcription, translation, or both, of the nucleic acid in a cell to which is delivered. Methods known to the skilled artisan can be used to construct expression constructs having the protein coding sequence operably linked with appropriate transcriptional/translational control signals. These methods include in vitro recombinant DNA techniques and synthetic techniques. For instance, see Sambrook et al., 1989, MOLECULAR CLONING: A LABORATORY MANUAL (Cold Spring Harbor Laboratory, New York).

A nucleic acid encoding one or more proteins of interest can be operatively associated with a variety of different promoter/regulator sequences. The promoter/regulator sequences can include a constitutive or inducible promoter, and can be used under the appropriate conditions to direct high level or regulated expression of the gene of interest. Particular examples of promoter/regulatory regions that can be used include the cytomegalovirus (CMV) promoter/regulatory region and the promoter/regulatory regions associated with the SV40 early genes or the SV40 late genes.

It also is within the scope of the present invention that the employed nucleic acid contains a plurality of protein-coding regions, combined on a single genetic construct under control of one or more promoters. The two or more protein-coding regions can be under the transcriptional control of a single promoter, and the transcript of the nucleic acid can comprise one or more internal ribosome entry sites interposed between the protein-coding regions. Thus, a myriad of different genes and genetic constructs can be utilized.

Methods of Making Particles

Further provided is a method of making the particle of the invention, the method comprising (1) providing (a) the matrix-forming agent, (b) a polyelectrolyte, (c) a first amphiphilic agent, (d) a first medium, (e) a second medium, and optionally providing a stabilizer; (2) mixing at least the matrix-forming agent, the first medium, and the second medium and optionally the polyelectrolyte, the first amphiphilic agent, and/or the stabilizer to give a first mixture; (3) emulsifying the first mixture to give a first emulsion; and (4) removing the first medium and thereby forming the particle, on a condition that the polyelectrolyte, the first amphiphilic agent, and the stabilizer are provided to at least one of the first medium, the second medium, the first mixture, the first emulsion, or the particle such that the polyelectrolyte and the first amphiphilic agent form the polyelectrolyte-amphiphilic agent adduct (see FIGS. 1A-1B).

In certain embodiments of the method, the polyelectrolyte, the first amphiphilic agent, and optionally the stabilizer are combined with the matrix-forming agent prior to mixing with the first medium or the second medium.

The term "first medium" as used herein denotes a solution, a micellar solution, an emulsion, or a suspension. In certain embodiments of the method, the first medium comprises an organic solvent. In certain embodiments of the method, the first medium comprises the organic solvent selected from the group consisting of chloroform, dichloromethane, tetrahydrofuran, acetone, ethanol, hexane, heptane, methylethylketone, propylene carbonate, ethyl acetate, acetylacetone, acetic anhydride, dimethylsulfoxide, dimethylformamide, acetonitrile and mixtures thereof. In certain embodiments, the organic solvent is provided as a ratio of at least two different organic solvents wherein the ratio influences a size of the particle. In one variant, the least two different organic solvents are tetrahydrofuran and chloroform provided at the ratio of about 0.1 to about 10 and the particle's diameter is about 370 nm to about 100 nm.

Emulsification can be performed by methods known in the art such as ultrasonication, high pressure homogenization, and microfluidization as described by Quintanar-Guerrero et al., supra.

Methods of preparing particles of the invention avoid using harsh conditions (e.g., extreme pH, elevated temperatures), which can cause degradation of the matrix-forming polymer and/or some biomaterials. Room temperature is preferred for steps involving addition of the biomaterial.

Preparations of coated magnetic field-responsive agent can be conducted at elevated temperatures in the absence of biomaterial.

In certain embodiments of the method, the second medium is a member selected from the group consisting of water, alcohols, and liquid hydrocarbons.

In certain embodiments, the method further comprises providing a biomaterial.

In certain embodiments of the method, the biomaterial is provided to at least one of the first mixture, the first emulsion and/or the particle. It may be added as is or in a co-solvent (for example, methotrexate (the biomaterial) can be added in dimethylsulfoxide (the co-solvent) to the first medium. Further, it can be incorporated in either component of the first medium, i.e. as a part of a solution, a micellar solution, an emulsion, or a suspension depending on solubility of the biomaterial in particular substances used.

In another embodiment, the method further comprises providing a coated magnetic field-responsive agent to at least one of the first medium, the second medium, and/or the first mixture. In certain embodiments, the coated magnetic field-responsive agent is provided by combining a magnetic field-responsive agent and a second amphiphilic agent in the presence of the first medium, the second medium, or the first mixture. Preferably, the coated magnetic field-responsive agent is dispersed in the first medium and mixed with the matrix-forming agent, the polyelectrolyte, the first amphiphilic agent, and the stabilizer prior to mixing with the second medium as shown in FIG. 5. In one variant of this embodiment, the method further comprises providing a biomaterial, wherein the biomaterial is provided to at least one of the first mixture, the first emulsion and/or the particle. Preferably, the biomaterial is provided to the particle, in such a manner that the biomaterial is in communication with the polyelectrolyte-first amphiphilic agent adduct, provided that the polyelectrolyte, the first amphiphilic agent, and the stabilizer are combined with the matrix-forming agent before mixing with the first medium.

Further provided is a method of making the magnetic particle of the invention, the method comprising: (i) providing the matrix-forming polymer, the coated magnetic field-responsive agent, a first medium and a second medium, and optionally providing a stabilizer; (ii) mixing at least the matrix-forming polymer, the first medium, and the second medium to give a second mixture; (iii) emulsifying the second mixture to give a second emulsion; and (iv) removing the first medium and thereby forming the particle, on a condition that the coated magnetic field-responsive agent and optionally the stabilizer are provided to at least one of the first medium, the second medium, or the second mixture. Preferably, the coated magnetic field-responsive agent is provided by combining the magnetic field-responsive agent and the second amphiphilic agent in a presence of the first medium, the second medium, or the second mixture. One variant of this embodiment includes further providing a biomaterial. The biomaterial can be provided to at least one of the second mixture, the second emulsion or the magnetic particle.

Methods of Delivery of Biomaterial to Target Cell or Target Tissue

Also provided is a method of delivery of a biomaterial to a target cell or a target tissue, the method comprising: administering the particle of the invention comprising the matrix-forming agent, polyelectrolyte-amphiphilic agent adduct, the coated magnetic field-responsive agent and the biomaterial; optionally providing a magnetic device associated with the target cell or the target tissue; applying a magnetic force to the particle; and guiding the particle by the magnetic force and thereby delivering the biomaterial to the target cell or the target tissue.

The source of magnetic field can be any source known in the art, e.g., an electromagnet. Magnetic field can be applied internally by placing a magnetic device inside a body in need of delivery of biomaterial; the magnetic field can be applied externally or as a combination of both.

Further provided is a method of delivery of a biomaterial to a target cell or a target tissue, the method comprising: administering the particle of the invention comprising the matrix-forming agent, the coated magnetic field-responsive agent, and the biomaterial, wherein the particle is free of the polyelectrolyte; providing a magnetic device associated with the target cell or the target tissue; applying a magnetic force to the particle; and guiding the particle by the magnetic force and thereby delivering the biomaterial to the target cell or the target tissue.

Also provided is a method of delivery of a biomaterial to a cell or a tissue, the method comprising: administering the particle of the invention comprising the matrix-forming agent, the polyelectrolyte-amphiphilic agent adduct, and the biomaterial, wherein the particle is free of the magnetic field-responsive agent; and delivering the biomaterial to the cell or tissue using the particle as a carrier, wherein the cell is optionally contacted with a transfection agent prior to said delivering.

Administering of the particle can be done, for example, by layering, spraying, pouring, injection, inhalation, or ingestion or a combination of any of the above.

The invention will be illustrated in more detail with reference to the following Examples, but it should be understood that the present invention is not deemed to be limited thereto.

EXAMPLES

Example 1

Preparation of a Coated Magnetic-Field Responsive Agent

The formulation of superparamagnetic biodegradable nanoparticles involves at least two steps: forming a long-chain carboxylic acid stabilized iron oxide nanocrystals and incorporation of the iron oxide nanocrystals in the biodegradable polymeric matrix of PLA-based nanoparticles formulated with PEI. The first step involves co-precipitation of ferric and ferrous chlorides in the presence of aqueous base solution (NaOH, 0.1N) with subsequent coating with oleic acid, thus rendering the nanocrystal surface lipophilic (see De Cuyper, supra; and Khalafalla supra). The obtained stabilized iron oxide nanocrystals were separated by extraction or centrifugation/magnetic sedimentation with subsequent resuspension in chloroform or a mixture of chloroform and tetrahydrofuran.

1 ml of an aqueous solution containing 65 mg of $FeCl_3$ hexahydrate, 32 mg of $FeCl_2$ tetrahydrate and 50 mg of Pluronic F-68 (as an optional stabilizer) (BASF Corp.) were rapidly mixed with 10 ml aqueous solution of NaOH (0.1M). Next, 200 mg of oleic acid were added dropwise, and the mixture was degassed in argon. The mixture was heated to 90° C. in a water bath for 5 min and cooled to room temperature. The mixture in a form of a suspension was vortexed with 5 ml of $CHCl_3$ to extract thus formed iron oxide nanocrystals, and the bottom layer was further used to prepare nanoparticles.

Preparation of Nanoparticles

Biodegradable matrix-forming polymer (polylactide) and PEI were incorporated into the iron oxide dispersion in the organic medium, and the organic phase thus obtained is emulsified in water followed by the organic solvent's evaporation (emulsification-solvent evaporation or the emulsification solvent-diffusion method) and nanoparticles filtration as in the example below.

200 mg of PLA (D, L-PLA (70-120 KDa) Sigma), 50 mg of Pluronic F-68 (BASF Corp.), 100 mg of PEI (25 KDa; Aldridge) were dissolved in 5 ml of iron oxide suspension in $CHCl_3$ as described above. The organic solution was added to 15 ml of distilled water pre-cooled to 0° C., and the mixture was emulsified by sonication on the ice bath. $CHCl_3$ was removed by rotavaporation at 30° C. The particles were filtered through 6 µm Whatman paper filter. The size of the nanoparticles was found to be 302 nm and remained stable for at least one week. The iron content in the nanoparticle suspension was found to be 74% with only 2.4% localized outside the nanoparticles indicating a high yield of the applied magnetite entrapment procedure (see FIGS. 1A-1B). FIG. 1C is a transmission electron micrograph of nanoparticles containing magnetite. The micrograph was taken without sample staining and magnetite appears as dark grains.

Nanoparticles that do not contain magnetic field-responsive agent can be prepared similarly using an organic phase devoid of iron oxide suspension: 200 mg of PLA (D, L-PLA (70-120 KDa) Sigma), 50 mg of Pluronic F-68 (BASF Corp.), 100 mg of PEI (25 KDa; Aldridge) were dissolved in 5 ml $CHCl_3$. The organic solution was added to 15 ml of distilled water pre-cooled to 0° C., and the mixture was emulsified by sonication on the ice bath. $CHCl_3$ was removed by rotavaporation at 30° C. The particles were filtered through 6 µm Whatman paper filter.

Figure 3:
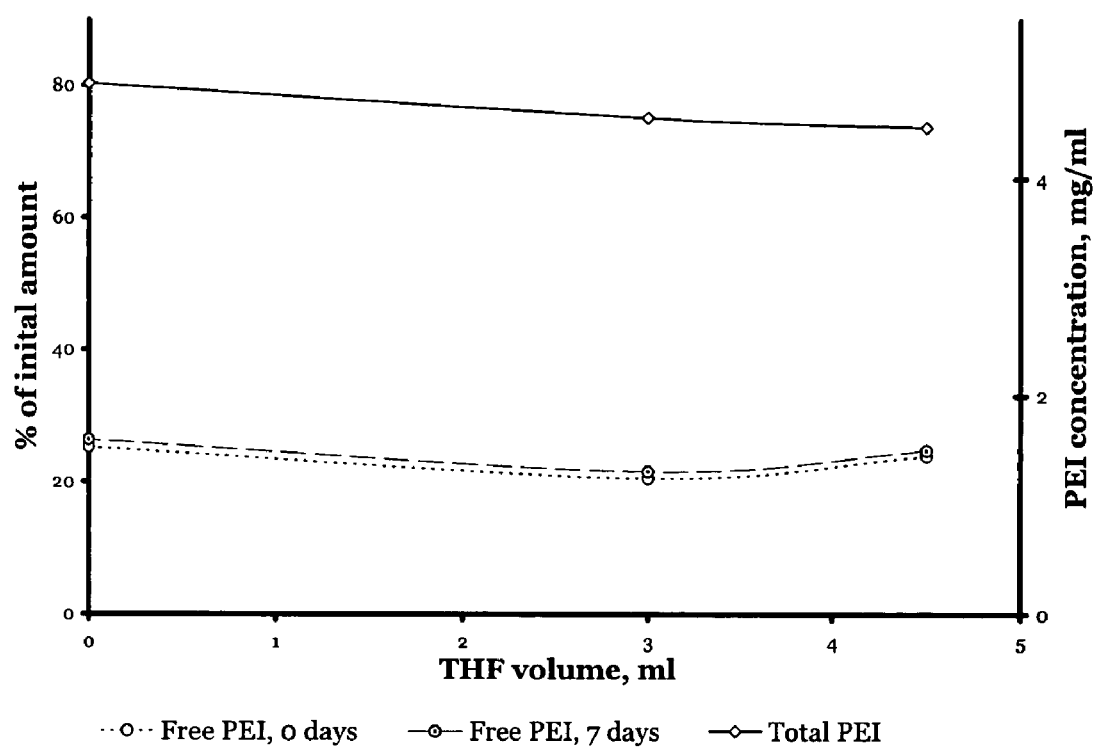
FIG. 3 is a graph showing the extent and stability of PEI association with magnetic NP as a function of the organic phase composition.

The total amount of PEI initially taken was determined in the formulation with only 13.5% localized outside the nanoparticles; the escape of PEI from the nanoparticles was slow resulting in about 30% localized outside the nanoparticles after 7 days (FIG. 3) as opposed to similarly prepared non-magnetic nanoparticles which did not include oleic acid and iron oxide in their composition.

Example 2

Use of Solvent to Control Size of Particle

Figure 2A:
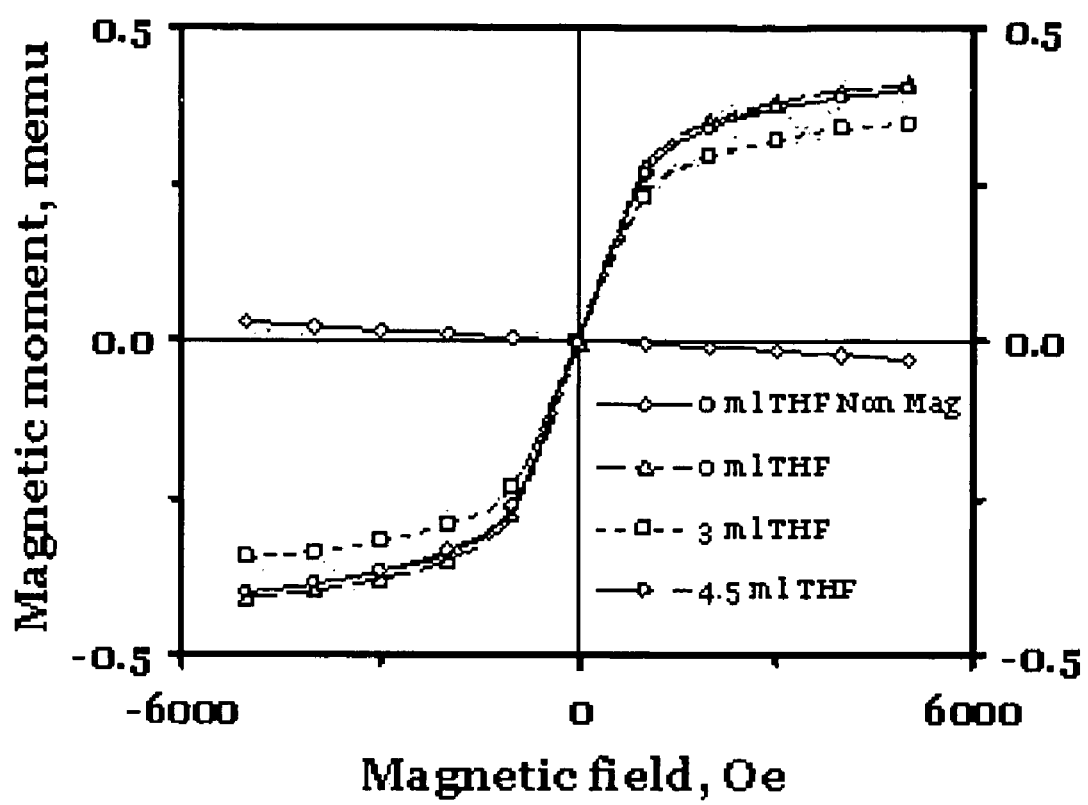
FIG. 2A is a graph demonstrating magnetic properties of nanoparticles prepared in various amounts of tetrahydrofuran (THF).
Figure 2B:
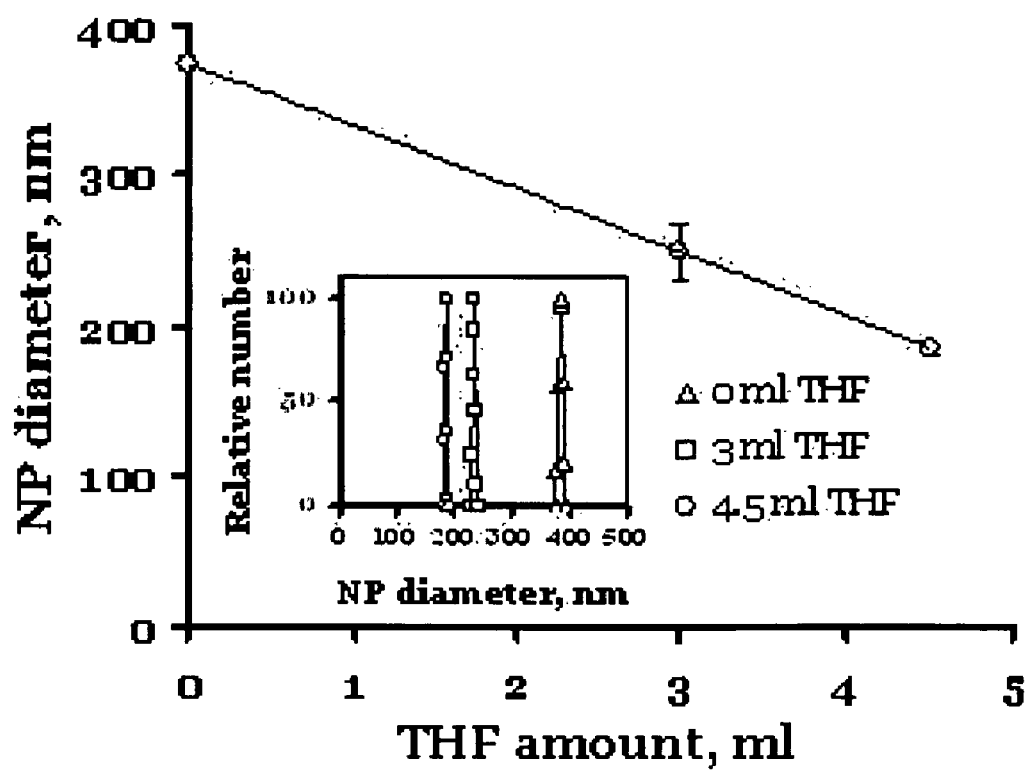
FIG. 2B is a graph showing the effect of the organic phase composition on the size of freshly prepared particles and size stability observed 7 days after particles' preparation.

Use of tetrahydrofuran (THF), a water-miscible solvent, in a mixture with chloroform to form the organic phase allows to considerably decrease the size of the resultant nanoparticles, thus making possible to optimize the nanoparticle uptake by a given cell type without affecting the amounts of the structural components in the formulation (i.e. PLA, PEI, $Fe_3O_4$, oleic acid) and the colloidal stability of the dispersion. Therefore, one can independently control size and surface charge, which is unachievable in complexes prepared by simply combining DNA and PEI. The effect of varying the volume of THF and chloroform (the organic phase composition) on particle magnetic behavior and size is shown in FIGS. 2A and 2B. The total volume of the tetrahydrofuran/chloroform mixture was kept constant and equal to 6.0 ml.

All magnetic formulations: 0 ml THF (large NP, LNP), 3 ml THF (medium NP, MNP), and 4.5 ml THF (small NP, SNP)) exhibit superparamagnetic behavior. A non-magnetic formulation of large NP included as a control is diamagnetic. FIG. 2B demonstrates a decrease in the nanoparticle size linear with the THF amount in the organic phase.

Example 3

Gene Transfer Efficiency and Cell Toxicity

Figure 4A:
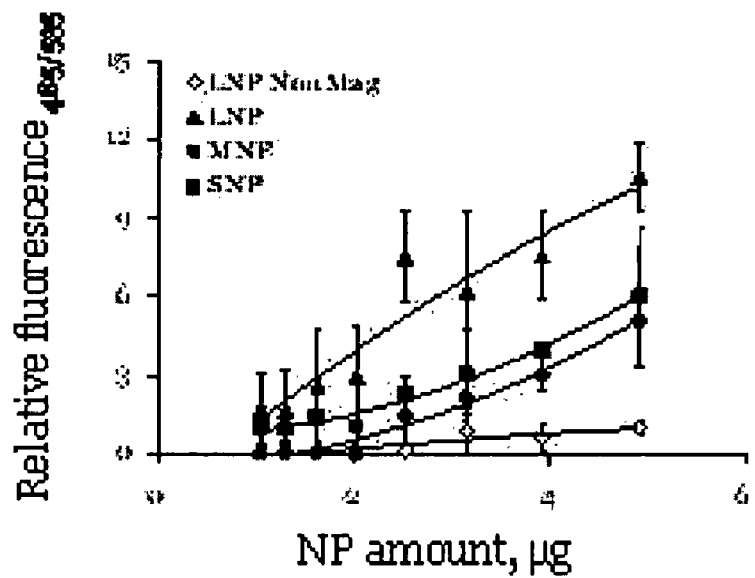
FIG. 4A is a graph demonstrating relative fluorescence measured at 485 nm/535 nm as a function of a nanoparticle amount in A 10 cells, wherein nanoparticles were prepared with iron oxide in 0 ml THF (large nanoparticles, LNP), 3 ml THF (medium nanoparticles, MNP), and 4.5 ml THF (small nanoparticles, SNP) and in 0 ml THF, large nanoparticles without iron oxide (LNP Non Mag, used herein as a control).
Figure 4B:
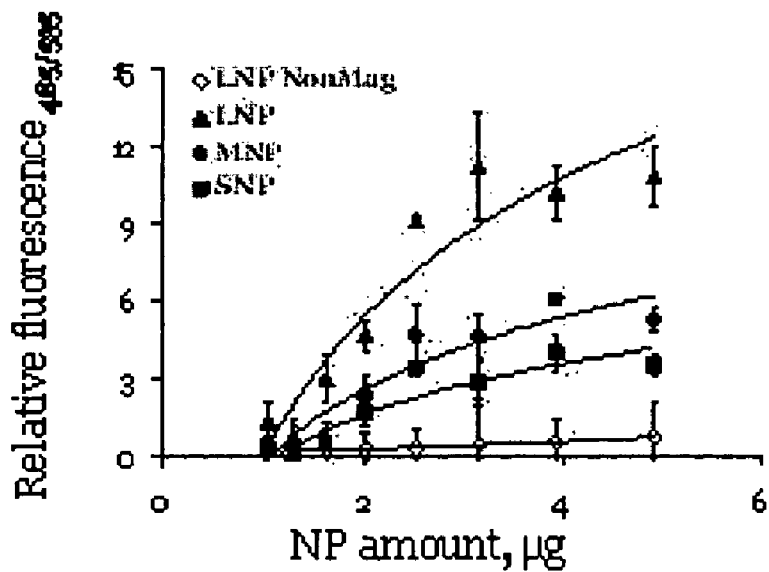
FIG. 4B is a graph demonstrating relative fluorescence measured at 485 nm/535 nm as a function of a nanoparticle amount in BAEC cells.
Figure 4C:
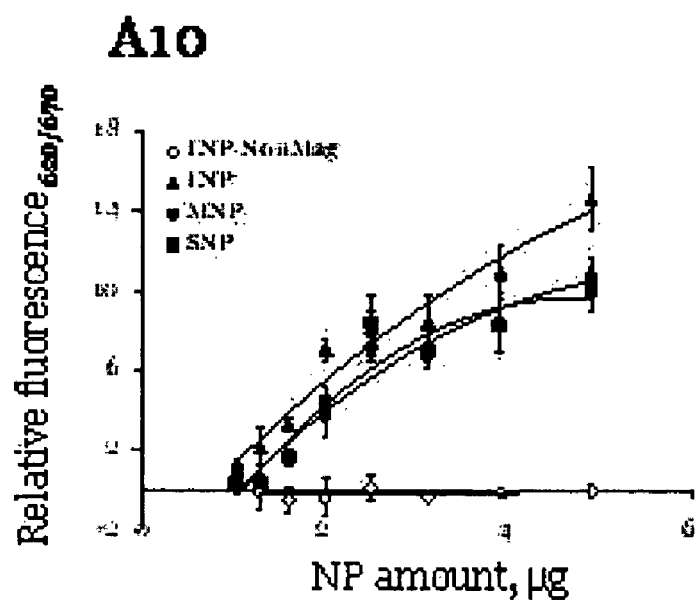
FIG. 4C is a graph demonstrating relative fluorescence measured at 650 nm/670 nm as a function of a nanoparticle amount in A 10 cells.
Figure 4D:
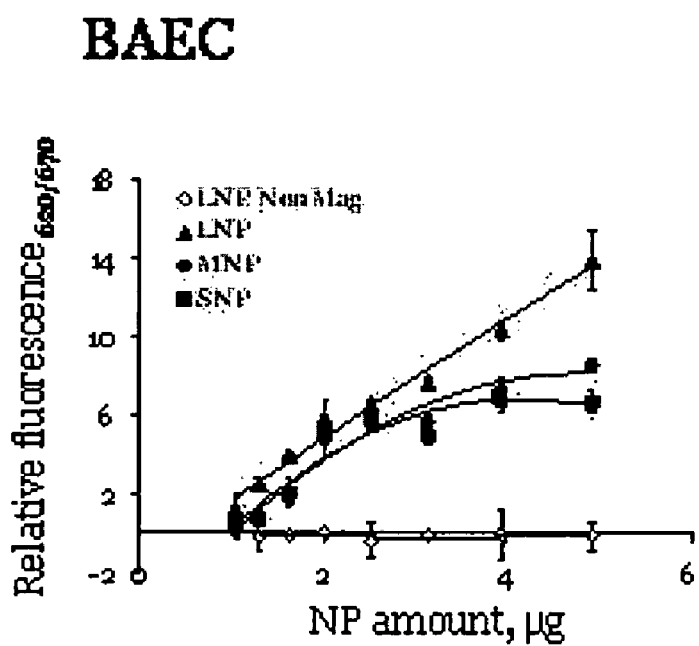
FIG. 4D is a graph demonstrating relative fluorescence measured at 650 nm/670 nm as a function of a nanoparticle amount in BAEC.
Figure 4E:
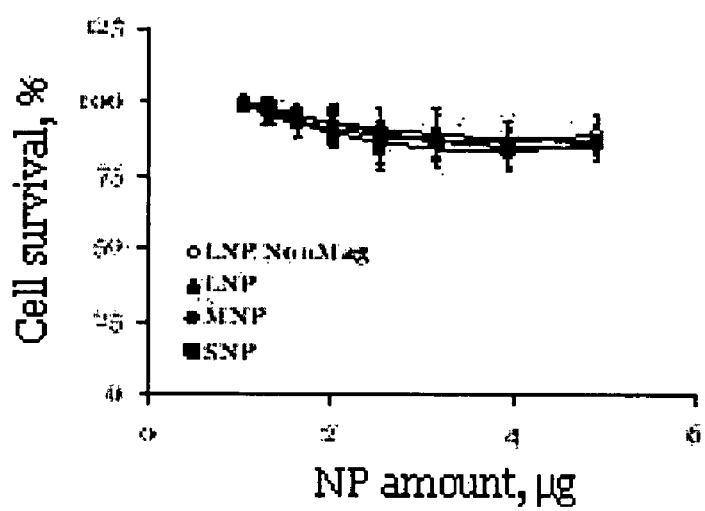
FIG. 4E is a graph demonstrating cells survival as a function of a nanoparticle amount in A10 cells.
Figure 4F:
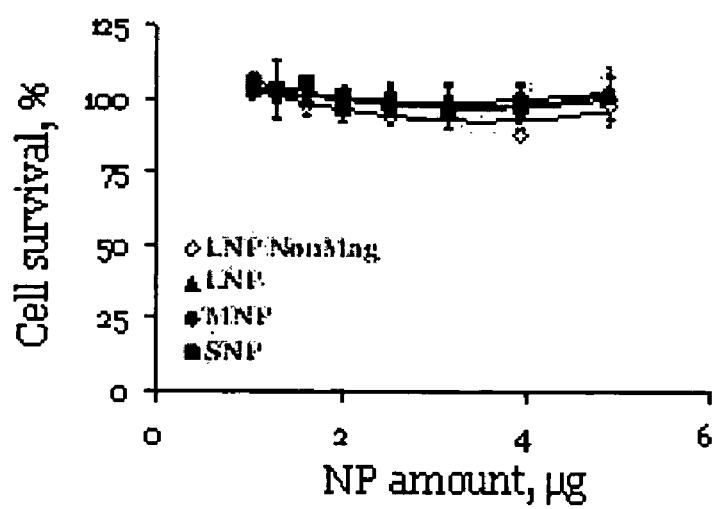
FIG. 4F is a graph demonstrating cells survival as a function of a nanoparticle amount in BAEC cells.

Next, particles were studied for transfection of cells in culture. Three kinds of magnetically responsive particles were prepared and complexed with DNA at different PEI: DNA ratios In all experiments, nanoparticles were complexed with 0.25 µg GFP-encoding DNA plasmid per well in 5% glucose for 30 min, then mixed 1:4 with cell culture medium supplemented with 10% serum and applied to cells for 10 min with magnetic field. Their transfection efficiency, as well as nanoparticles uptake and toxicity was studied in cultured rat aortic smooth muscle and bovine aortic endothelial cells (A10 and BAEC, respectively) using non-magnetic particles as a control. Gene expression, NP uptake and cell survival were determined by measuring fluorescence at 485/535 nm, 620/670 nm and with the Alamar Blue assay, respectively, at 2 day time point. The results are presented in FIGS. 4A-4F. Magnetically responsive formulations resulted in high levels of gene product as opposed to non-magnetic nanoparticles (FIGS. 4A and B) in correlation with their cellular uptake (FIGS. 4C and D). All formulations exhibited low toxicity in cell culture in the examined amount range (FIGS. 4E and F).

In another experiment, bovine aortic endothelial cells (BAEC) were seeded on day-1 ($2 \times 10^4$/well, on four 24-well plate). The cells were washed 2 times (2×1 hr) with the unsupplemented medium (DMEM) on day 0 prior to transfection. DNA stock solution (0.55 ml) was slowly added to 0.55 ml of complexants diluted to provide 0.25 g DNA per well complexed at predetermined theoretical charge ratios and left for 30 min. 0.125 ml of the unsupplemented medium was added to each well followed by 0.125 ml preparation; the cells were incubated at 37° C., while one plate was placed at a time on the magnet (15 min) (the other kept at a distance from it). The medium was then replaced with fresh pre-warmed medium supplemented with 10% FCS. The cells were observed for transfection after 24 hr.

Figure 5A:
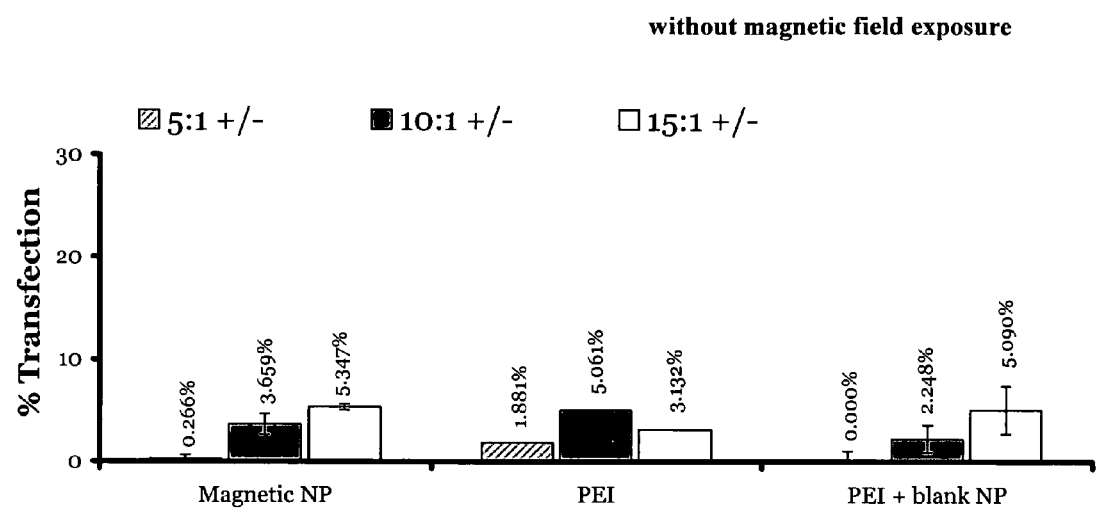

The nanoparticles and PEI showed comparable transfection of BAEC cells in culture with DNA encoding for green fluorescent protein when applied without use of external magnetic field (FIG. 5A), whereas the transfection efficacy of the magnetic nanoparticles applied in the presence of a permanent magnet (FIG. 5B) was substantially increased as compared to both control formulations and the magnetic nanoparticles applied in the absence of the magnet (FIG. 5A).

Similar effect of the magnetic field on the transfection efficacy was also observed in A10 cells in culture.

Notably, the magnetic NP were able to effectively transfect cells in presence of 10% and 80% serum apparently due to their protective effect against DNA enzymatic degradation, whereas practically no transfection was found when DNA: PEI complex was added to the cells in the presence of serum for the same time period.

Example 4

Preparation of Nanoparticles Comprising Biomaterial

Nanoparticles were prepared as described in Example 1 and Example 2. DNA encoding for green fluorescent protein was used as a biomaterial. DNA in 5% glucose aqueous solution was added to nanoparticles suspended in 5% aqueous glucose solution, incubated at RT for 30 min; and gently mixed by up and down pipetting.

The nanoparticles were shown to completely bind DNA at theoretical nitrogen:phosphate ratios above 10 and 5 for glucose 5% solution and MES 0.1 M (pH=6.5) buffer, respectively, used as complexation medium.

Next, particles were studied for transfection of cells in culture with and without use of external magnetic field.

Three kinds of particles were prepared at three different PEI:DNA theoretic ratios (5:1; 10:1; and 15:1).

Figure 5B:
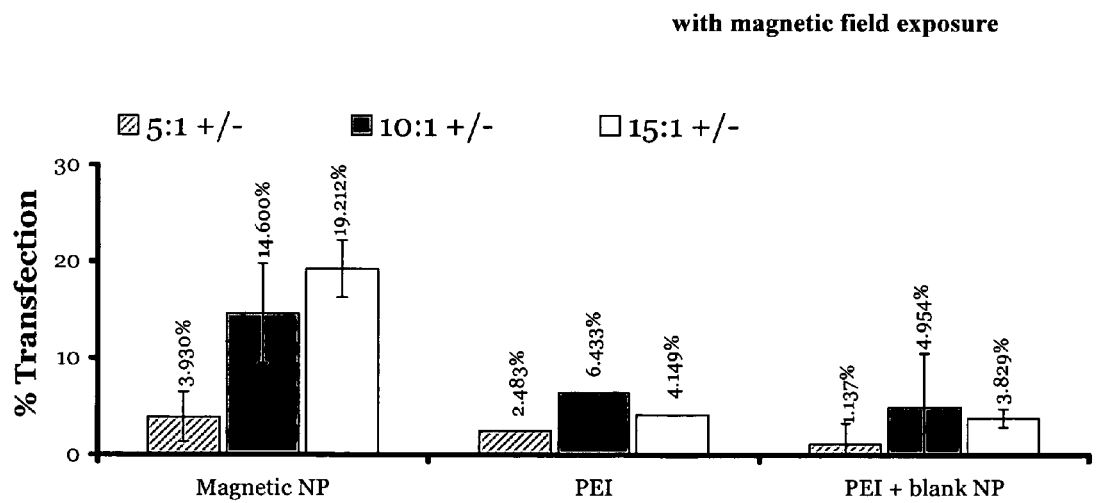

One kind of particles denoted in FIGS. 5A and 5B as "magnetic NP" included magnetic nanoparticles comprising PLA, PEI, oleic acid, iron oxide coated with oleic acid and DNA (shown in FIGS. 5A and 5B as magnetic NP). Serving as controls, "PEI" included particles comprising PEI and DNA and "PEI+blank NP" were particles consisting of free PEI mixed with DNA in the presence of blank PLA particles.

Next, particles were added to BAEC cells and transfection was measured in the absence and presence of external magnetic field as shown in FIGS. 5A and 5B respectively.

Example 5

Preparation of Nanoparticles

An alternative procedure provides nanoparticles with a higher magnetite loading. 5.5 ml aqueous solution containing 300 mg $FeCl_3$ hexahydrate, and 150 mg $FeCl_2$ tetrahydrate was rapidly mixed with 4.5 ml aqueous solution of NaOH (1.0 M). The precipitate was separated on a magnet and suspended in 2 ml ethanol with oleic acid (150 mg). The mixture was degassed in argon and heated to 90° C. in a water bath for 5 min. 4 ml water was added dropwise upon gentle stirring, the oleic acid-coated iron oxide was precipitated on a magnet, and the liquid phase was carefully aspirated. The precipitate was washed with 4 ml ethanol to remove excess oleic acid and resuspended in 6 ml chloroform. 200 mg PLA ($_{D,L}$-PLA, 70-120 K from Sigma) and 100 mg oleic acid were dissolved in the iron oxide suspension in chloroform. 100 mg PEI (25 K from Aldrich) was dissolved in 4 ml water and 1 ml EtOH. The organic phase was emulsified in 15 ml water by sonication while adding the PEI solution. The organic solvents were removed by rotavaporation at 25° C. The particles were filtered through 1.0 μm glass fiber filter and dialyzed against deionized water at 4° C. for 24 hr with several water replacements using 300,000 Da cut-off dialysis membrane.

The use of higher amounts of iron salts in the particle preparation resulting in increased magnetite loading in the final nanoparticles provides formulations with substantially higher magnetic responsiveness.

While the invention has been described in detail and with reference to specific examples thereof, it will be apparent to one skilled in the art that various changes and modifications can be made therein without departing from the spirit and scope thereof.

REFERENCES

1. Plank C, Anton M, Rudolph C, Rosenecker J, Krotz F. Enhancing and targeting nucleic acid delivery by magnetic force. Expert Opin Biol Ther. 2003; 3:745-58.

2. Plank C, Schillinger U, Scherer F, Bergemann C, Remy J S, Krotz F, Anton M, Lausier J, Rosenecker J. The magnetofection method: using magnetic force to enhance gene delivery. Biol. Chem. 2003; 384:737-47.

3. Plank C, Scherer F, Schillinger U, Bergemann C, Anton M. Magnetofection: enhancing and targeting gene delivery with superparamagnetic nanoparticles and magnetic fields. J Liposome Res. 2003; 13:29-32.

4. Krotz F, Wit C, Sohn H Y, Zahler S, Gloe T, Pohl U, Plank C. Magnetofection-A highly efficient tool for antisense oligonucleotide delivery in vitro and in vivo. Mol Ther. 2003; 7:700-10.

5. Scherer F, Anton M, Schillinger U, Henke J, Bergemann C, Kruger A, Gansbacher B, Plank C. Magnetofection: enhancing and targeting gene delivery by magnetic force in vitro and in vivo. Gene Ther. 2002; 9:102-9.

6. Krotz F, Sohn H Y, Gloe T, Plank C, Pohl U. Magnetofection potentiates gene delivery to cultured endothelial cells. J Vasc Res. 2003; 40(5):425-434.

7. De Cuyper M, Joniau M. Magnetoliposomes. Formation and structural characterization. Eur Biophys J 1988; 15:311-9;

8. Khalafalla S E. Magnetic fluids, Chemtech 1975, September: 540-7.

9. Forrest M L, Koerber J T, Pack D W. A degradable polyethylenimine derivative with low toxicity for highly efficient gene delivery. Bioconjug Chem. 2003 September-October; 14(5):934-40

10. Gosselin M A, Guo W, Lee R J. Efficient gene transfer using reversibly cross-linked low molecular weight polyethylenimine. Bioconjug Chem. 2001 November-December; 12(6):989-94.)

11. Kumar M NR. Nano and microparticles as controlled drug delivery devices. J Pharm Pharmaceut Sci 2000; 3:234-58).

12. Quintanar-Guerrero et al., Preparation techniques and mechanisms of formation of biodegradable nanoparticles from preformed polymers. Drug Dev Ind Pharm 1998; 24:1113-28).

13. Arias J L, et al., Synthesis and Characterization of Poly(ethyl-2-cyanoacrylate) Nanoparticles with a Magnetic Core. J of Controlled Release 77 (2001) 309-321.

14. Gómez-Lopera S A, et al., Synthesis and Characterization of Spherical Magnetite/Biodegradable Polymer Composite Particles. J. of Colloid and Interface Science 240, 40-47 (2001).

15. Messai I, et al., Elaboration of Poly(ethyleneimine) Coated Poly(D, L-lactic acid) Particles. Effect of Ionic Strength on the Surface Properties and DNA Binding Capabilities. Colloids and Surfaces B: Biointerfaces 32 (2003) 293-305.

16. Igartua M., et al., Development and Characterization of Solid Lipid Nanoparticles Loaded with Magnetite. Int'l. J. of Pharmaceutics 233 (2002) 149-157.

17. Hyeon T., Chemical Synthesis of Magnetic Nanoparticles. The Royal Society of Chemistry 2003, Chem. Commun., 2003, 927-934.

18. Sullivan Ow M M, et al., Development of a Novel Gene Delivery Scaffold Utilizing Colloidal Gold-Polyethylenimine Conjugates for DNA Condensation. Gene Therapy (2003) 10, 1882-1890.

19. Ito R., et al., Magnetic Granules: A Novel System for Specific Drug Delivery to Esophageal Mucosa in Oral Administration. Int'l. J. of Pharmaceutics, 61 (1990) 109-117.

20. Müller R H, et al., Cytotoxicity of Magnetite-Loaded Polylactide, Polylactide/Glycolide Particles and Solid Lipid Nanoparticles. Int'l. J. of Pharmaceutics 138 (1996) 85-94.

21. Wagner E., et al., Coupling of Adenovirus to Transferrin-Polylysine/DNA Complexes Greatly Enhances Receptor-Mediated Gene Delivery and Expression of Transfected Genes. Proc. Nat'l. Acad. Sci. USA Vol. 89 pp. 6099-6103, July 1992 Biochemistry.

What is claimed is:

1. A particle comprising:
   a matrix-forming polymer; and
   a polyelectrolyte-amphiphilic agent complex formed by an ionic association of a polyelectrolyte with a first amphiphilic agent and having a $C_4$-$C_{24}$ hydrocarbon chain, wherein the polyelectrolyte-amphiphilic agent complex is in physical communication with the matrix-forming polymer; the particle further comprising a coated magnetic field-responsive agent comprising a magnetic field-responsive agent in communication with a second amphiphilic agent, wherein the coated magnetic field-responsive agent is in communication with the matrix-forming polymer.

2. The particle of claim 1, wherein the matrix-forming polymer is selected from the group consisting of poly(ester), poly(urethane), poly(alkylcyanoacrylate), polyanhydride, polyethylenevinyl acetate, poly(lactone), poly(styrene), poly(amide), poly(acrylonitrile), poly(acrylate), poly(methacrylate), poly(orthoester), poly(ether-ester), poly(tetrafluoroethylene), mixtures thereof and copolymers of corresponding monomers.

3. The particle of claim 2, wherein the poly(ester) is a member selected from the group consisting of poly(lactide), poly(glycolide), poly(lactide-co-glycolide), poly(ε-caprolactone), poly(dioxanone), poly(hydroxybutyrate), and poly(ethylene terephthalate).

4. The particle of claim 1, wherein the polyelectrolyte-amphiphilic agent complex is poly(ethyleneimine) carboxylate.

5. The particle of claim 1, wherein the polyelectrolyte is a member selected from the group consisting of poly(ethyleneimine), poly(allylamine), poly(lysine), poly(arginine), poly(spermine), poly(spermidine) and derivatives thereof.

6. The particle of claim 1, wherein the first amphiphilic agent is a member selected from the group consisting of fatty acids, lipids and salts thereof.

7. The particle of claim 6, wherein the first amphiphilic agent is a $C_{12}$-$C_{24}$ carboxylic acid.

8. The particle of claim 7, wherein the first amphiphilic agent is oleic acid.

9. The particle of claim 1, wherein the second amphiphilic agent is a member selected from the group consisting of fatty acids, lipids and salts thereof.

10. The particle of claim 1, wherein the magnetic field-responsive agent is a member selected from the group consisting of iron, cobalt, nickel, alloys of iron, alloys of cobalt, alloys of nickel, oxides of iron, oxides of cobalt, oxides of nickel, and mixtures of one or more iron compounds with one or more other metal compounds;
   wherein the one or more iron compounds are selected from the group consisting of Fe(II) oxide, Fe(II) hydroxide, Fe(III) oxide and Fe(III) hydroxide; and
   wherein the one or more other metal compounds are selected from the group consisting of Co(II) oxide, Co(II) hydroxide, Mn(II) oxide, Mn(II) hydroxide, Cu(II) oxide, Cu(II) hydroxide, Ni(II) oxide, Ni(II) hydroxide, Cr(III) oxide, Cr(III) hydroxide, Gd(III) oxide, Gd(III) hydroxide, Dy(III) oxide, Dy(III) hydroxide, Sm(III) oxide and Sm(III) hydroxide.

11. The particle of claim 10, wherein the magnetic field-responsive agent is $Fe_3O_4$, gamma-$Fe_2O_3$, or a mixture thereof.

12. The particle of claim 1, further comprising a biomaterial in communication with at least one of the polyelectrolyte-amphiphilic agent complex or the matrix-forming polymer.

13. The particle of claim 12, wherein the biomaterial is a member selected from the group consisting of a nucleic acid, a protein, a peptide, an oligonucleotide, an antibody, an antigen, a viral vector, a bioactive polypeptide, a polynucleotide encoding a bioactive polypeptide, a cell regulatory small molecule, a gene therapy agent, a gene transfection vector, a receptor, a cell, a drug, a drug delivering agent, an antimicrobial agent, an antibiotic, an antimitotic, an antisecretory agent, an anti-cancer chemotherapeutic agent, steroidal and non-steroidal anti-inflammatories, a hormone, a proteoglycan, a glycosaminoglycan, a free radical scavenger, an iron chelator, an antioxidant, an imaging agent, and a radiotherapeutic agent.

14. The particle of claim 13, wherein the biomaterial is a nucleic acid and the nucleic acid is DNA or RNA or a synthetic analogue of either of these.

15. The particle of claim 1, further comprising a stabilizer.

16. The particle of claim 15, wherein the stabilizer is a member selected from the group consisting of ethylene oxide-propylene oxide block copolymers, poloxamine, poly(sorbate), sorbitan ester, alkyl polyethylene glycol ether, and fatty acid polyethylene glycol ester.

17. The particle of claim 1, wherein the particle has a diameter of about 5 nm to about 10 microns.

18. A particle comprising:
   a matrix-forming polymer;
   a polyelectrolyte-amphiphilic agent adduct comprising a first $C_{12}$-$C_{24}$ carboxylate group, wherein the first $C_{12}$-$C_{24}$ carboxylate group is in physical communication with the matrix-forming polymer;
   a second amphiphilic agent comprising a second $C_{12}$-$C_{24}$ carboxylate group in communication with the matrix-forming polymer; and
   a magnetic-field responsive agent in communication with the second $C_{12}$-$C_{24}$ carboxylate group.

19. The particle of claim 18, further comprising a stabilizer.

20. The particle of claim 18, further comprising a biomaterial in communication with the polyelectrolyte-amphiphilic agent adduct and optionally with the matrix-forming polymer.

21. A method of delivery of a biomaterial to a target cell or a target tissue, the method comprising:

administering a particle comprising (i) a matrix-forming polymer, (ii) a polyelectrolyte-amphiphilic agent complex formed by an ionic association of a polyelectrolyte with a first amphiphilic agent and having a $C_4$-$C_{24}$ hydrocarbon chain, wherein the polyelectrolyte-amphiphilic agent complex is in physical communication with the matrix-forming polymer, (iii) a coated magnetic field-responsive agent comprising a magnetic field-responsive agent in communication with a second amphiphilic agent, wherein the coated magnetic field-responsive agent is in communication with the matrix-forming polymer, and (iv) the biomaterial, said biomaterial being in communication with at least one of the polyelectrolyte-amphiphilic agent complex or the matrix-forming polymer;

optionally providing a magnetic device associated with the target cell or the target tissue;

applying a magnetic force to the particle; and guiding the particle by the magnetic force and thereby delivering the biomaterial to the target cell or the target tissue.

* * * * *